US012357464B2

(12) United States Patent
Bohenick et al.

(10) Patent No.: US 12,357,464 B2
(45) Date of Patent: Jul. 15, 2025

(54) MAMMALIAN BONY IMPLANT AND ANCHORS INSERTER SYSTEM

(71) Applicant: Osseus Fusion Systems, Dallas, TX (US)

(72) Inventors: John Bohenick, Troy, MI (US); Chase D. Tipping, Dallas, TX (US); Kyle Blaskovich, Dallas, TX (US); Andrew Schindler, Dallas, TX (US)

(*) Notice: Subject to any disclaimer, the term of this patent is extended or adjusted under 35 U.S.C. 154(b) by 683 days.

(21) Appl. No.: 17/744,596

(22) Filed: May 13, 2022

(65) Prior Publication Data

US 2023/0248524 A1 Aug. 10, 2023

Related U.S. Application Data

(63) Continuation-in-part of application No. 17/665,373, filed on Feb. 4, 2022, now Pat. No. 11,963,882.

(51) Int. Cl.
*A61F 2/30* (2006.01)
*A61F 2/44* (2006.01)
*A61F 2/46* (2006.01)

(52) U.S. Cl.
CPC ........ *A61F 2/30749* (2013.01); *A61F 2/4455* (2013.01); *A61F 2/4611* (2013.01); *A61F 2002/30405* (2013.01); *A61F 2002/30622* (2013.01)

(58) Field of Classification Search
CPC .................. A61F 2/44–447; A61F 2/4611
See application file for complete search history.

(56) References Cited

U.S. PATENT DOCUMENTS

| | | | | |
|---|---|---|---|---|
| 2010/0292704 | A1* | 11/2010 | Stoffel | A61F 2/4601 606/99 |
| 2013/0123925 | A1* | 5/2013 | Patterson | A61B 17/8033 623/17.16 |
| 2015/0173915 | A1* | 6/2015 | Laubert | A61F 2/4611 623/17.16 |
| 2019/0000638 | A1* | 1/2019 | Gilbride | A61F 2/447 |

FOREIGN PATENT DOCUMENTS

WO  WO-2017066475 A1 * 4/2017 ............. A61B 17/70

* cited by examiner

*Primary Examiner* — Nicholas J Plionis
(74) *Attorney, Agent, or Firm* — Merle W Richman, III

(57) ABSTRACT

Embodiments of the present invention provides systems and methods for deploying implants and anchors to treat one or more bony segments. A system may enable a User to insert an implant between adjacent bony segments and advance one or more bony anchors thereafter via the same system. Other embodiments may be described and claimed.

18 Claims, 25 Drawing Sheets

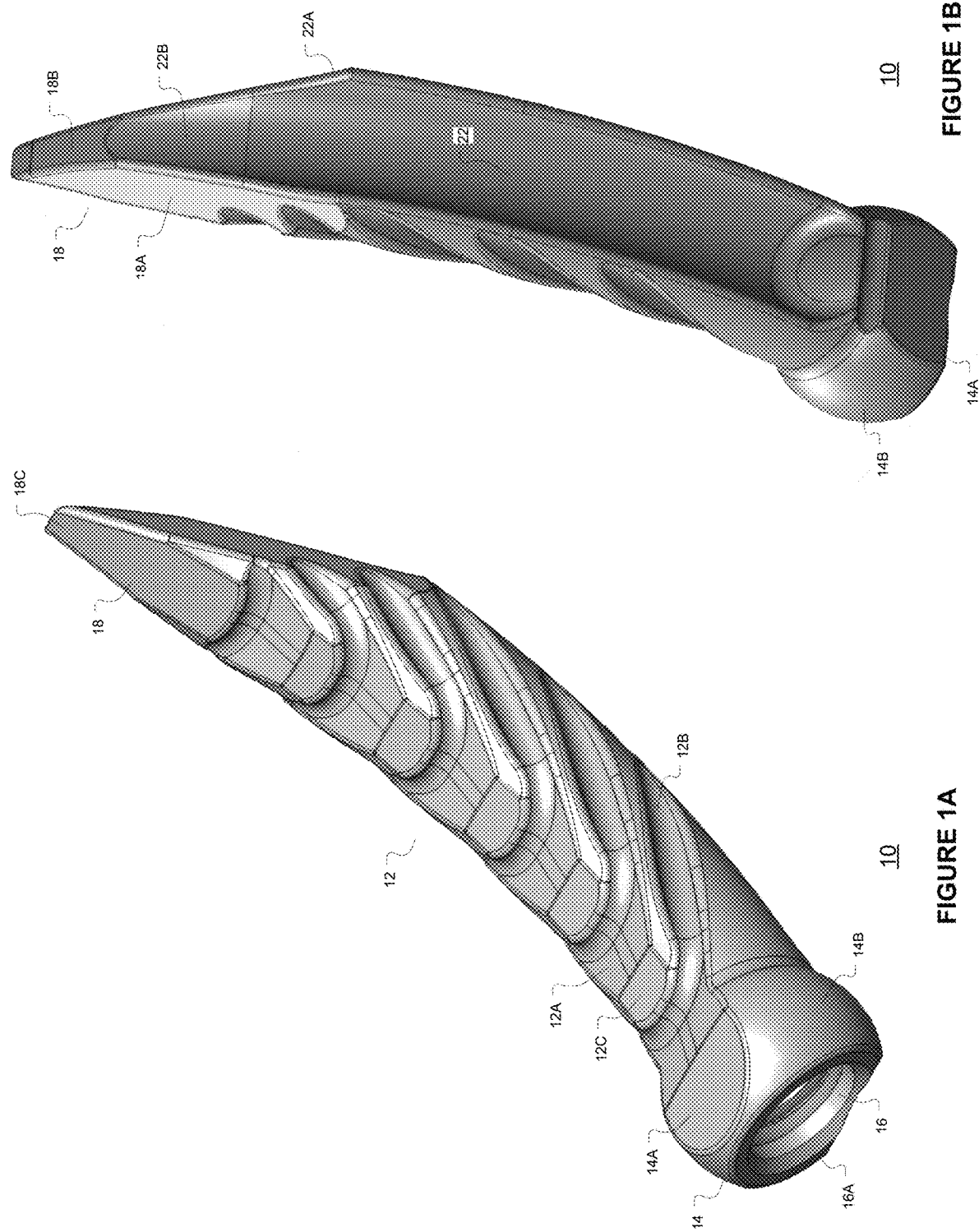

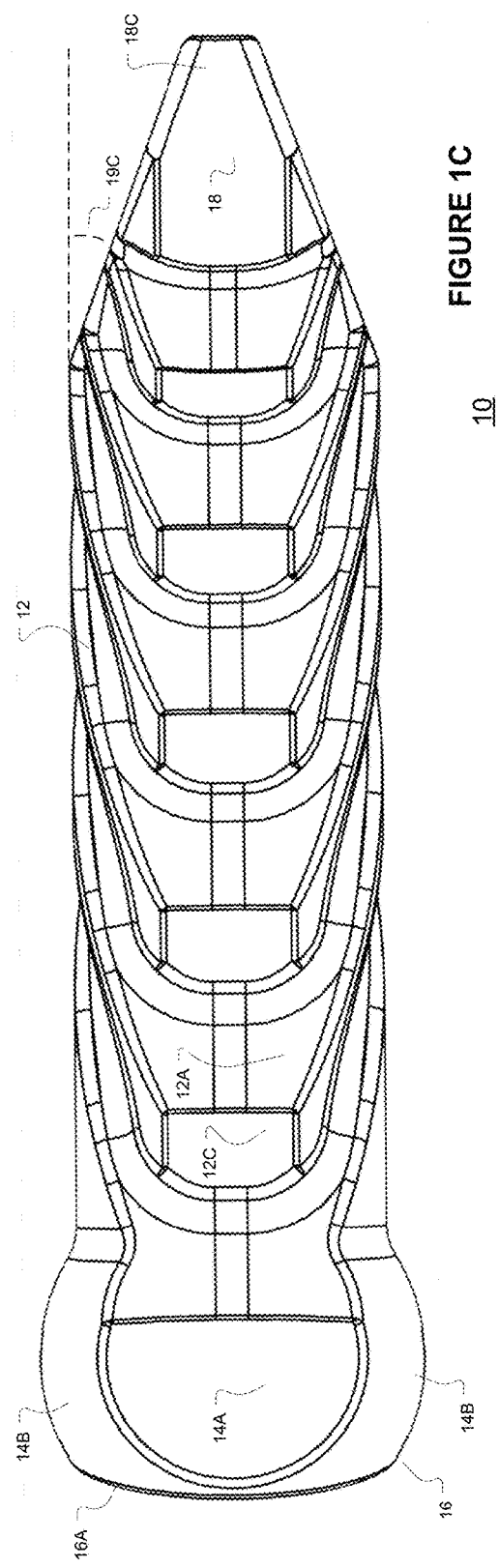

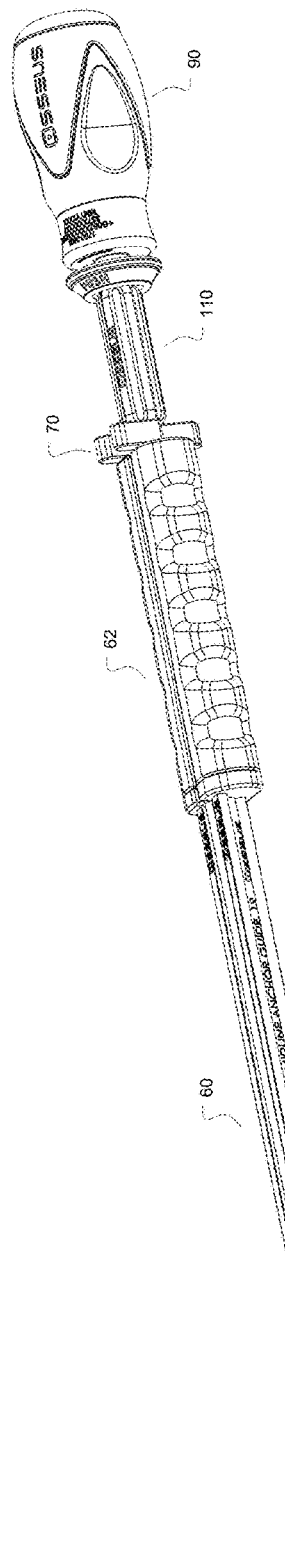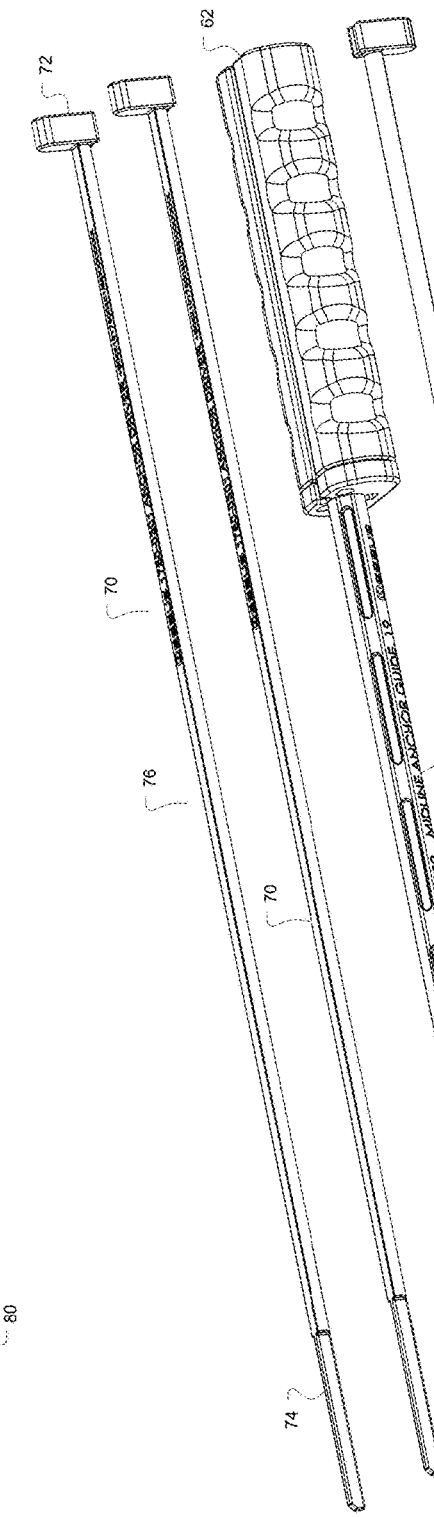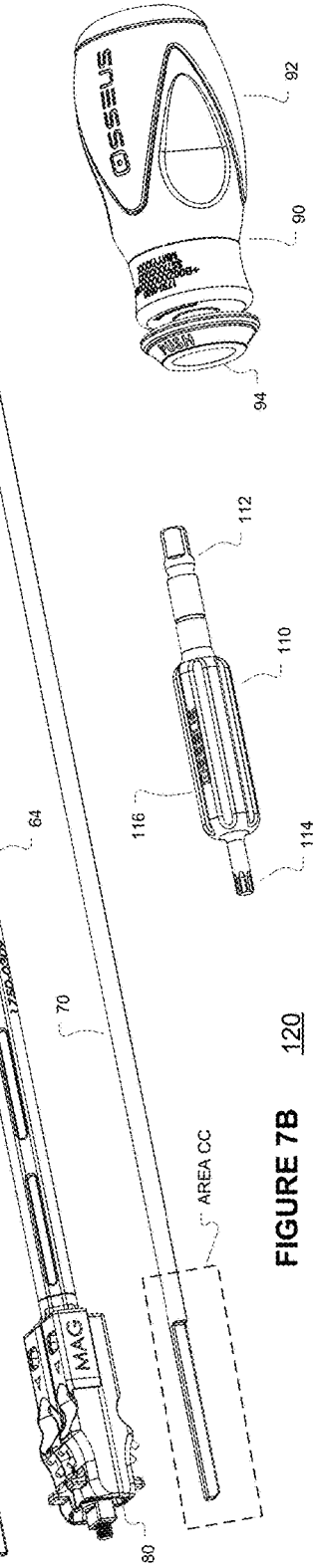
FIGURE 7A
FIGURE 7B

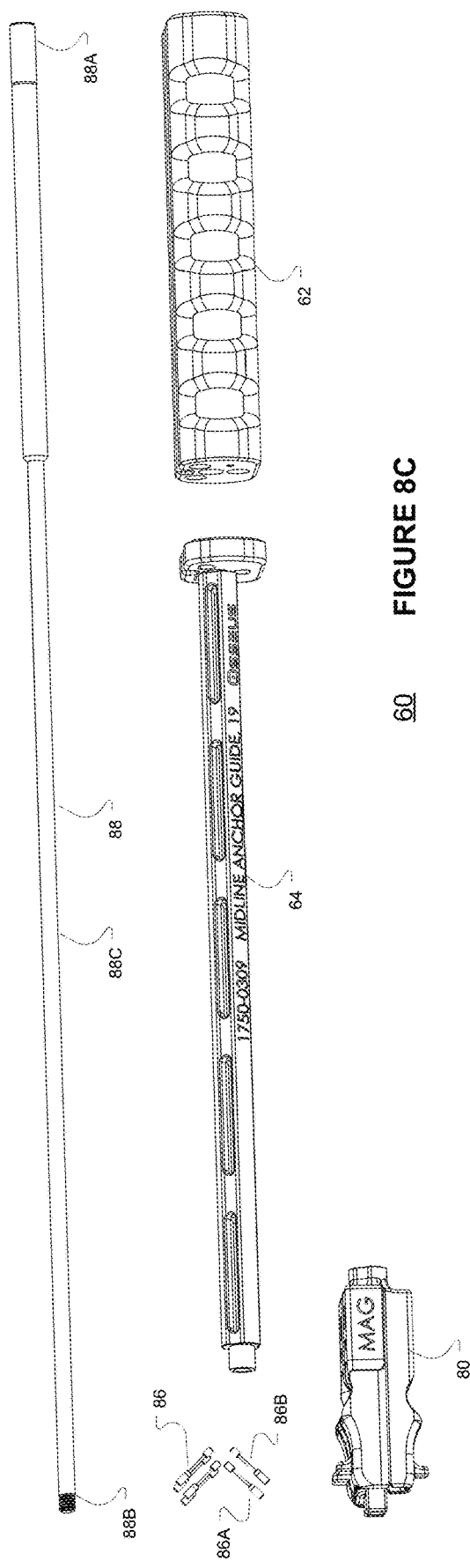
FIGURE 8C
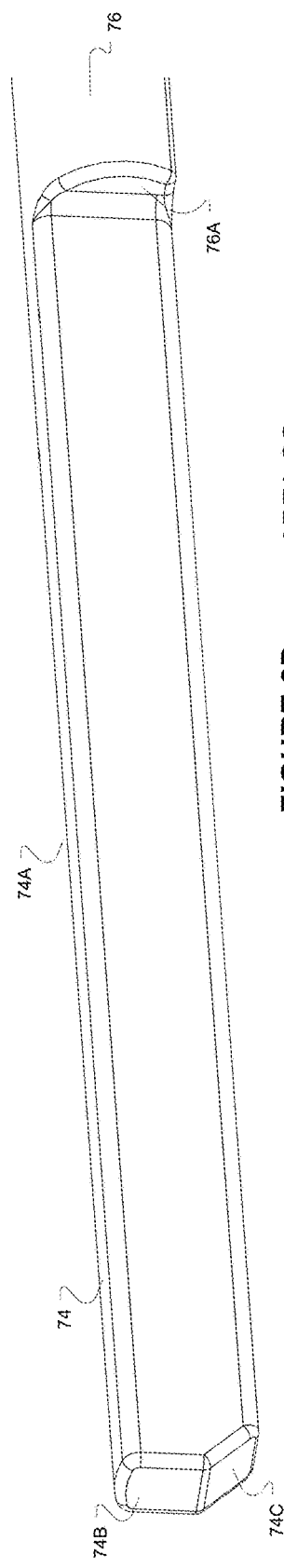
FIGURE 8D  AREA CC

AREA DD

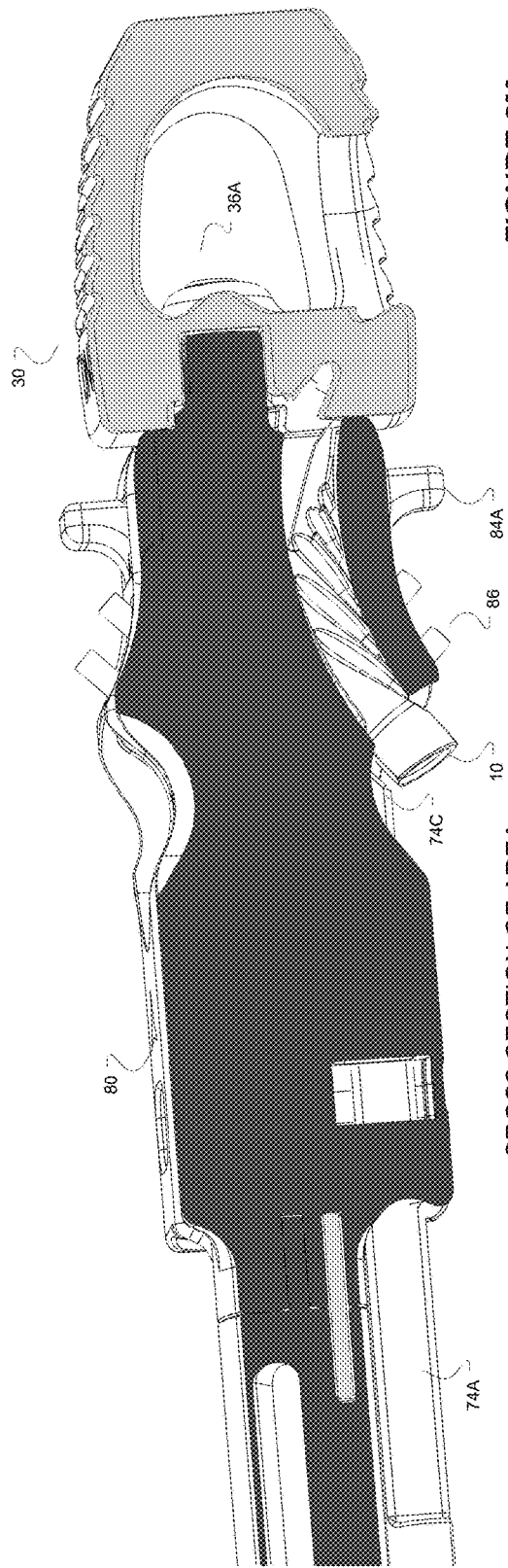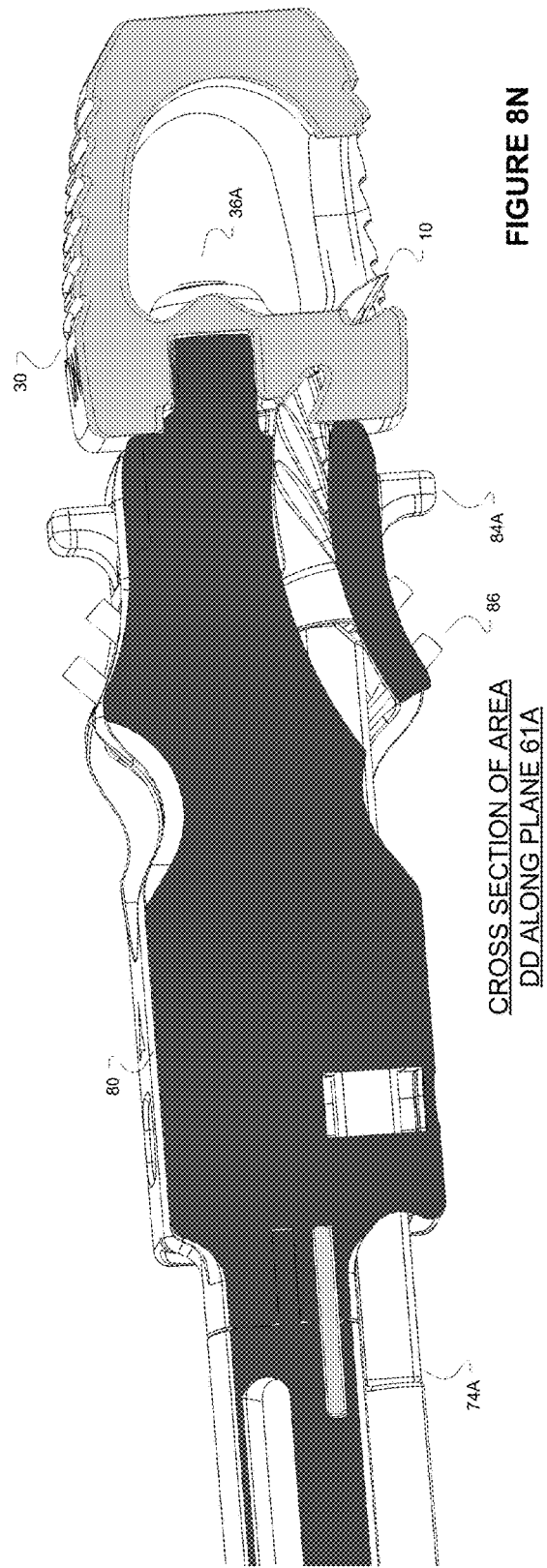

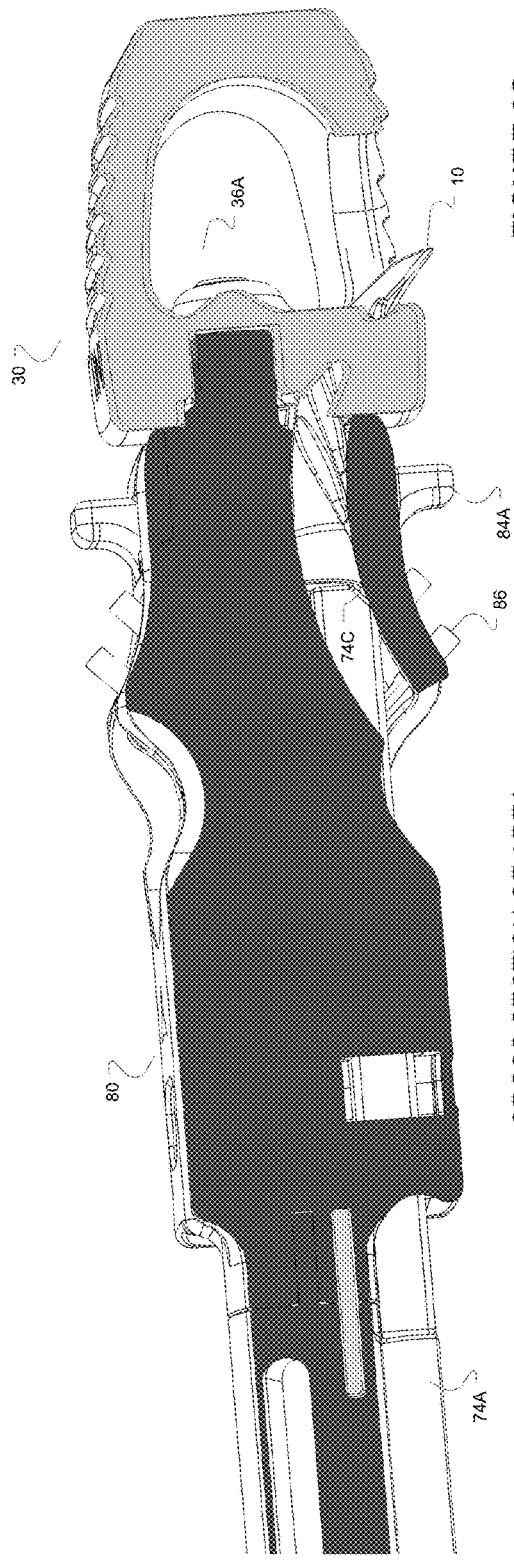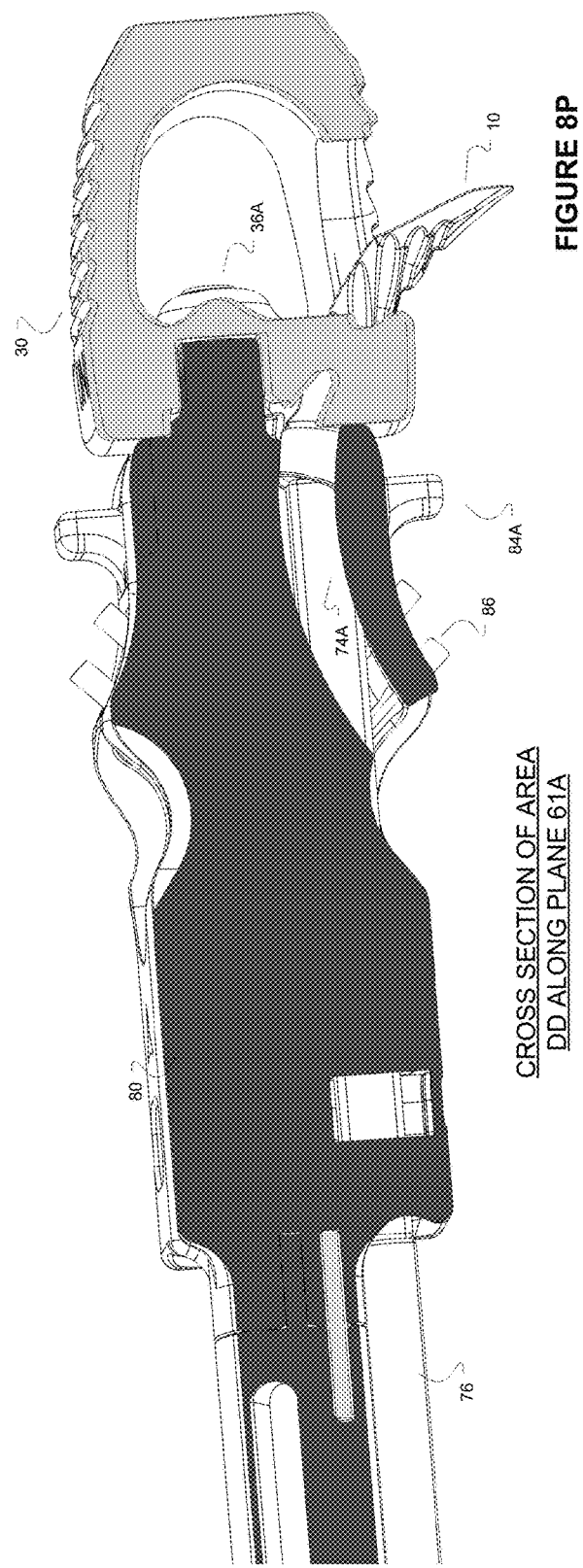

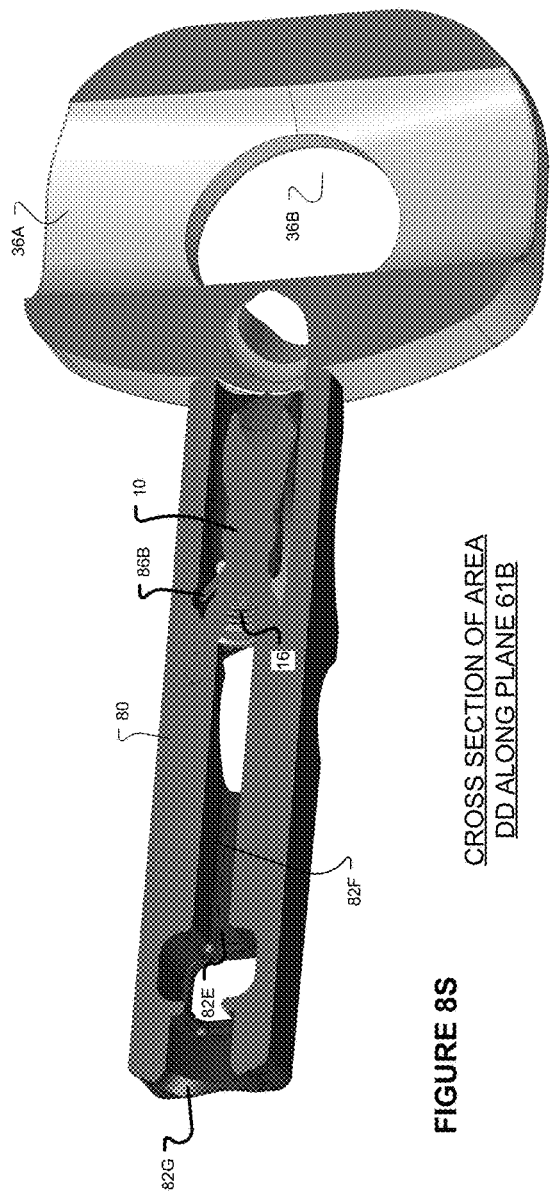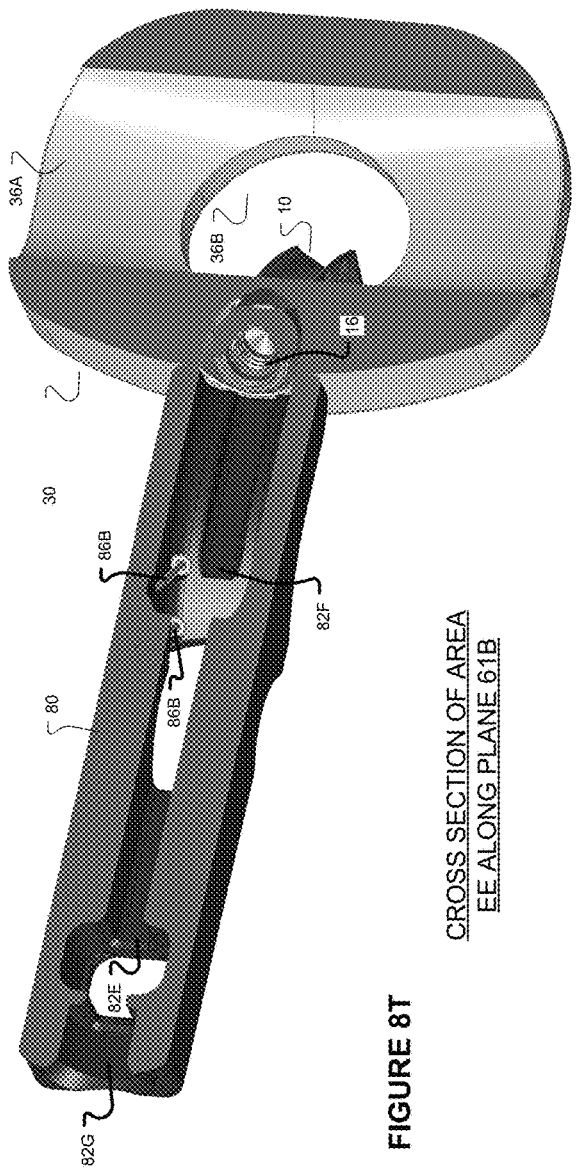
CROSS SECTION OF AREA DD ALONG PLANE 61B
FIGURE 8S
CROSS SECTION OF AREA EE ALONG PLANE 61B
FIGURE 8T

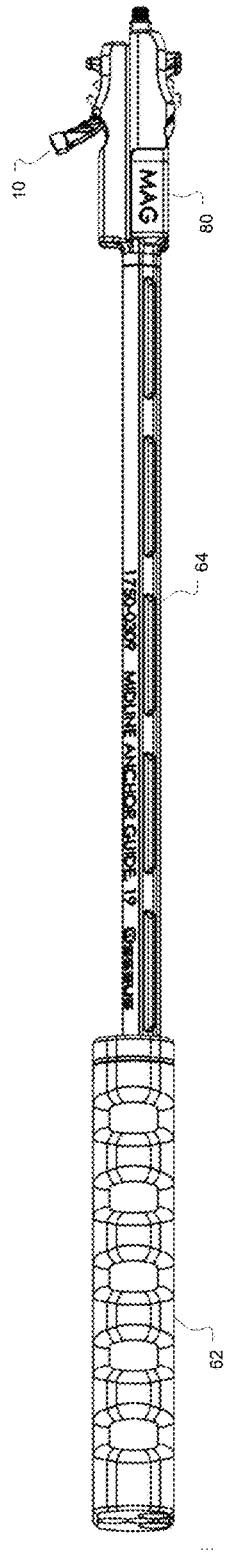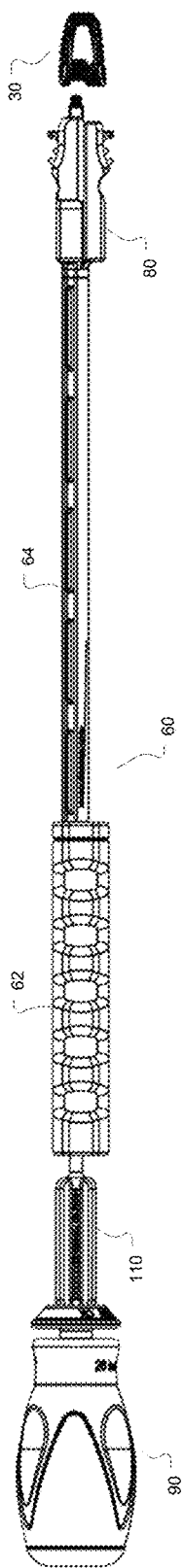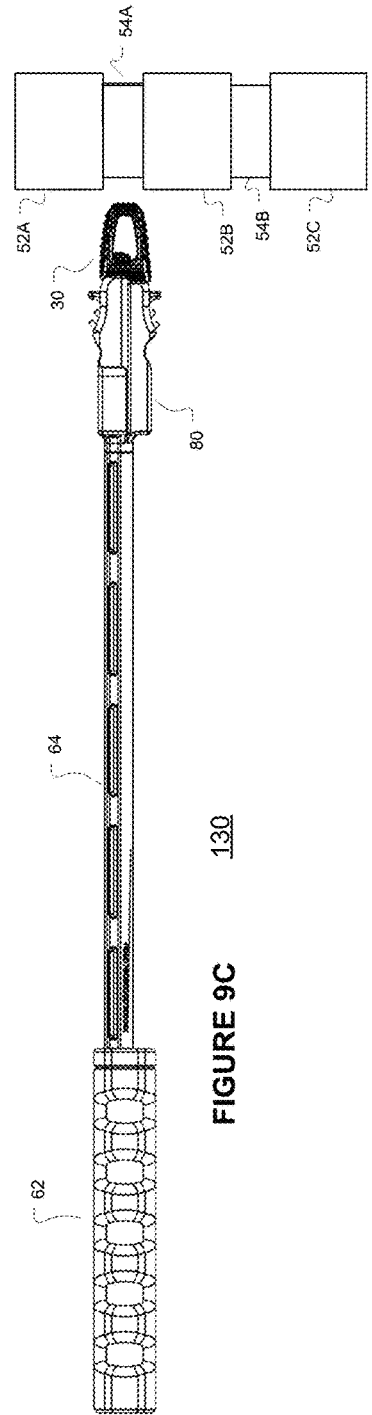
FIGURE 9A
FIGURE 9B
FIGURE 9C

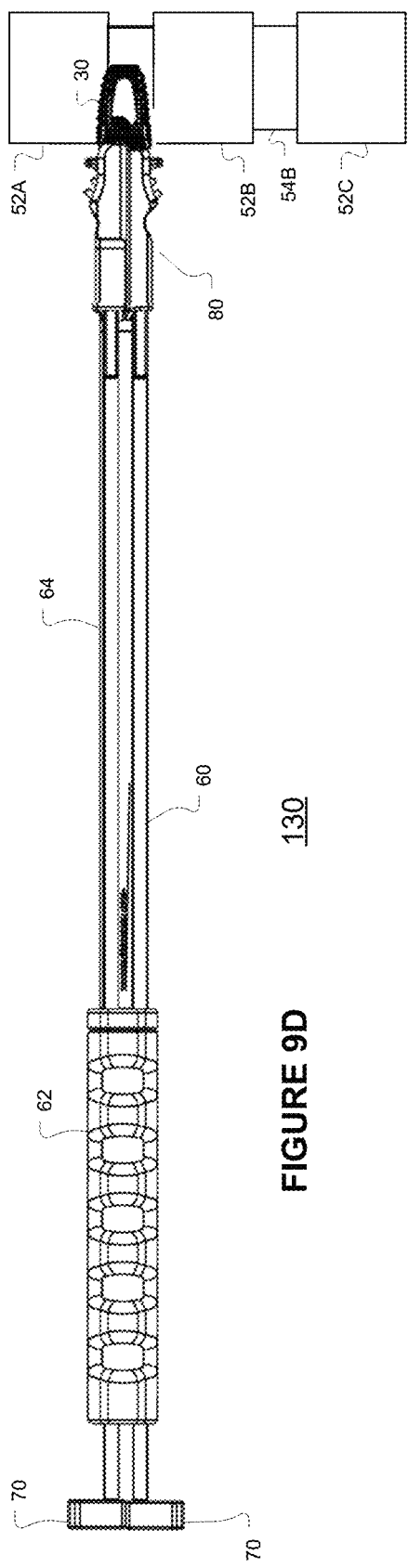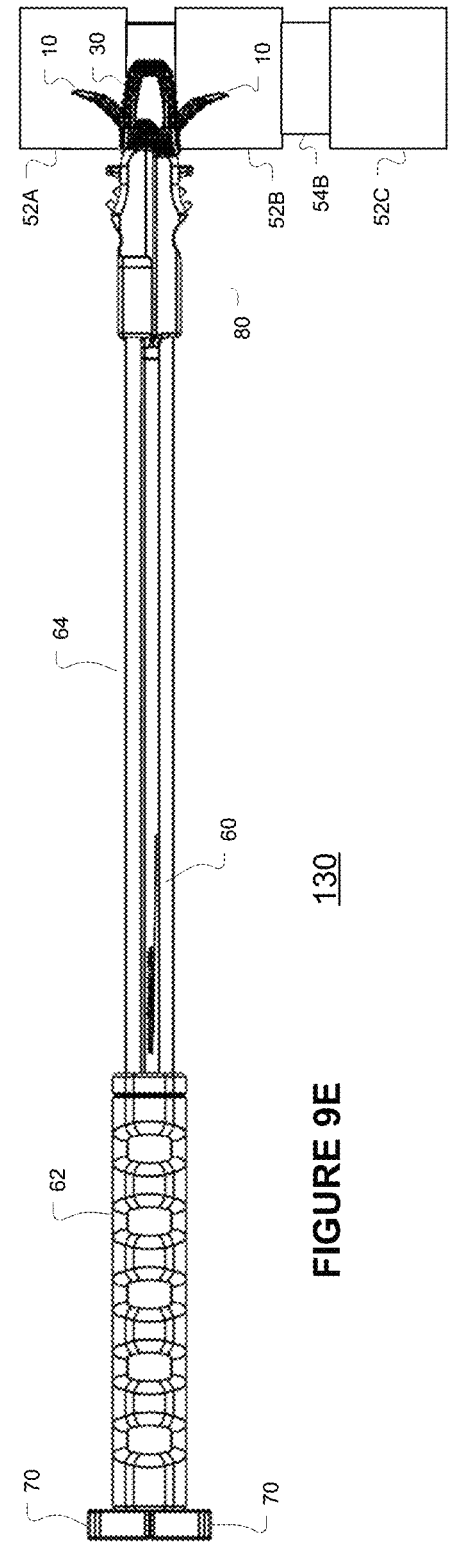

MAMMALIAN BONY IMPLANT AND ANCHORS INSERTER SYSTEM

TECHNICAL FIELD

Various embodiments described herein relate generally to treating mammalian bony segments, including systems and methods that help deploy implants and anchors to stabilize, maintain spacing between, or couple one or more mammalian bony segments.

BACKGROUND INFORMATION

It may be desirable to treat one or more bony segments via mammalian implants and bony anchor(s) to encourage bony fusion, stabilize, maintain spacing between, or couple the bony segments. The present invention provides systems and methods for deploying implants and anchors to treat one or more bony segments.

BRIEF DESCRIPTION OF THE DRAWINGS

FIG. 1A is a simplified isometric front drawing of a mammalian bony anchor (MBA) according to various embodiments.

FIG. 1B is a simplified isometric rear drawing of an MBA according to various embodiments.

FIG. 1C is a simplified top view of an MBA according to various embodiments.

FIG. 1D is a simplified bottom view of an MBA according to various embodiments.

FIG. 7A is an isometric simplified drawing of a combination implant and anchor inserter system (CIAIS) according to various embodiments.

FIG. 7B is an isometric simplified drawing of the removable elements of the CIAIS as shown in FIG. 7A according to various embodiments.

FIG. 8C is a simplified exploded side view of a combination implant and anchor inserter (CIAI) shown in FIG. 8A according to various embodiments.

FIG. 8D is a simplified drawing of area CC of an anchor impact element (AIE) of a CIAIS shown in FIG. 7B according to various embodiments.

FIG. 8M is a cross section drawing along plane 61A shown on FIG. 8A of area DD of a combination implant and anchor inserter (CIAI) coupled to an implant and a mammalian bony anchor nested therein with an anchor impact element withdrawn proximally according to various embodiments.

FIG. 8N is a cross section drawing along plane 61A shown on FIG. 8A of area DD of a combination implant and anchor inserter (CIAI) coupled to an implant and a mammalian bony anchor extending therefrom with an anchor impact element forwarded more distally according to various embodiments.

FIG. 8O is a cross section drawing along plane 61A shown on FIG. 8A of area DD of a combination implant and anchor inserter (CIAI) coupled to an implant and a mammalian bony anchor further extended therefrom with an anchor impact element forwarded further more distally according to various embodiments.

FIG. 8P is a cross section drawing along plane 61A shown on FIG. 8A of area DD of a combination implant and anchor inserter (CIAI) coupled to an implant and a mammalian bony anchor almost completely extended therefrom with an anchor impact element forwarded further more distally into the implant according to various embodiments.

FIG. 8S is a cross section drawing along plane 61B of area DD shown in FIG. 8A of a combination implant and anchor inserter (CIAI) coupled to an implant and an anchor nested completely therein according to various embodiments.

FIG. 8T is a cross section drawing along plane 61B of area DD shown in FIG. 8A of a combination implant and anchor inserter (CIAI) coupled to an implant and a mammalian bony anchor completely ejected therefrom according to various embodiments.

FIG. 9A is a side upside down drawing of a combination implant and anchor inserter (CIAI) with a mammalian bony anchor partially being inserted therein according to various embodiments.

FIG. 9B is a side drawing of a TLR, coupler, and combination implant and anchor inserter (CIAI) with mammalian bony anchors stored therein being coupled to an implant according to various embodiments.

FIG. 9C is a side drawing of a combination implant and anchor inserter (CIAI) coupled to an implant with mammalian bony anchors stored therein prior to implant insertion between adjacent bony segments according to various embodiments.

FIG. 9D is a side drawing of a combination implant and anchor inserter (CIAI) coupled to an implant with mammalian bony anchors stored therein and AIEs partially inserted therein where the implant is fully inserted between adjacent bony segments according to various embodiments.

FIG. 9E is a side drawing of AIEs fully inserted and combination implant and anchor inserter (CIAI) coupled to an implant and AIEs fully inserted therein where the mammalian bony anchors are fully implanted into adjacent bony segments and the implant fully inserted between adjacent bony segments according to various embodiments.

DETAILED DESCRIPTION

Figure 1E:
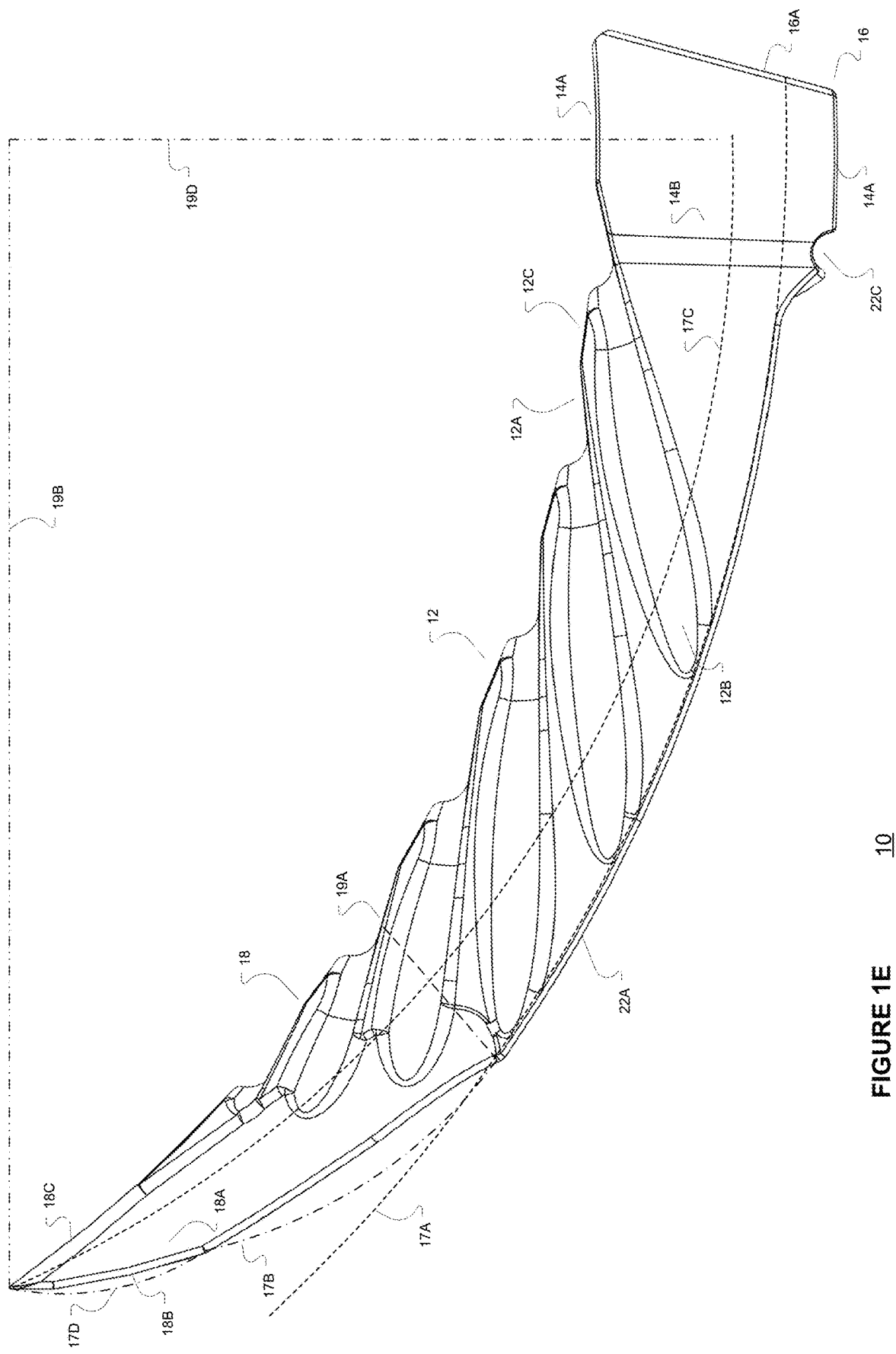
FIG. 1E is a simplified left side view of an MBA according to various embodiments.
Figure 1G:
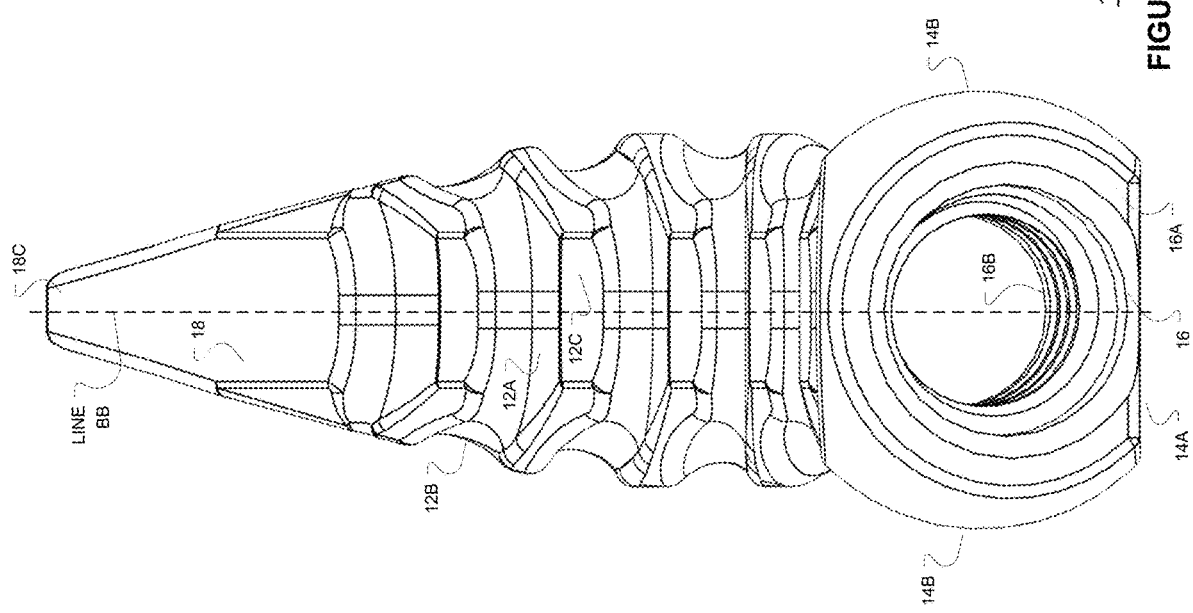
FIG. 1G is a simplified rear view of an MBA according to various embodiments.
Figure 1F:
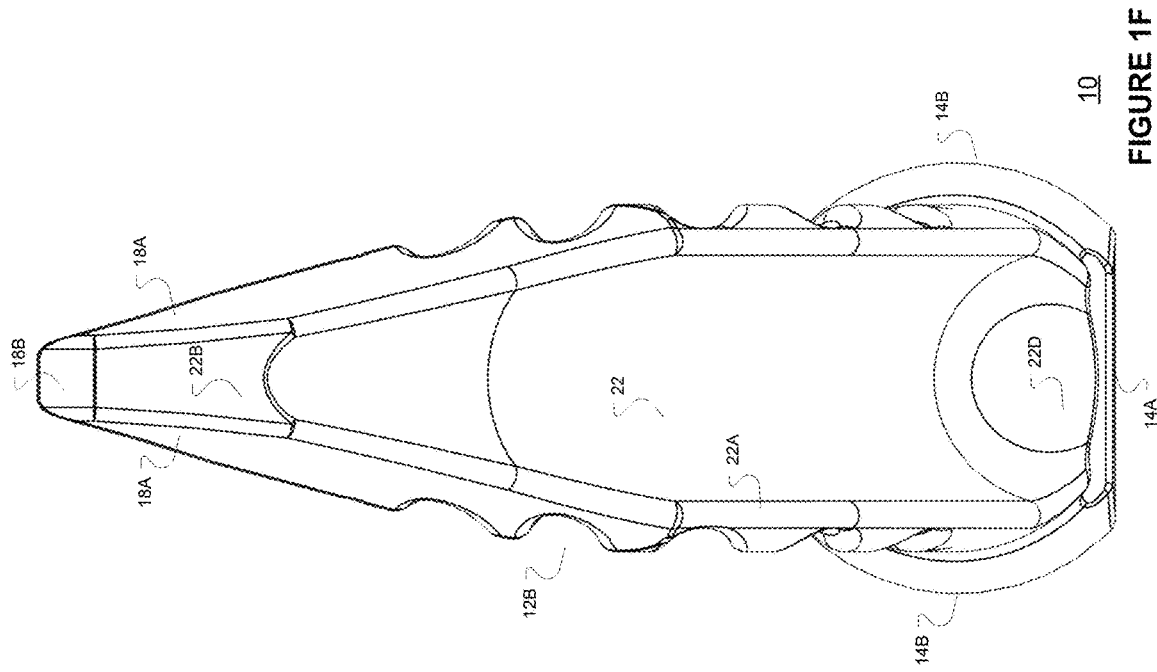
FIG. 1F is a simplified bottom front view of an MBA according to various embodiments.
Figure 1H:
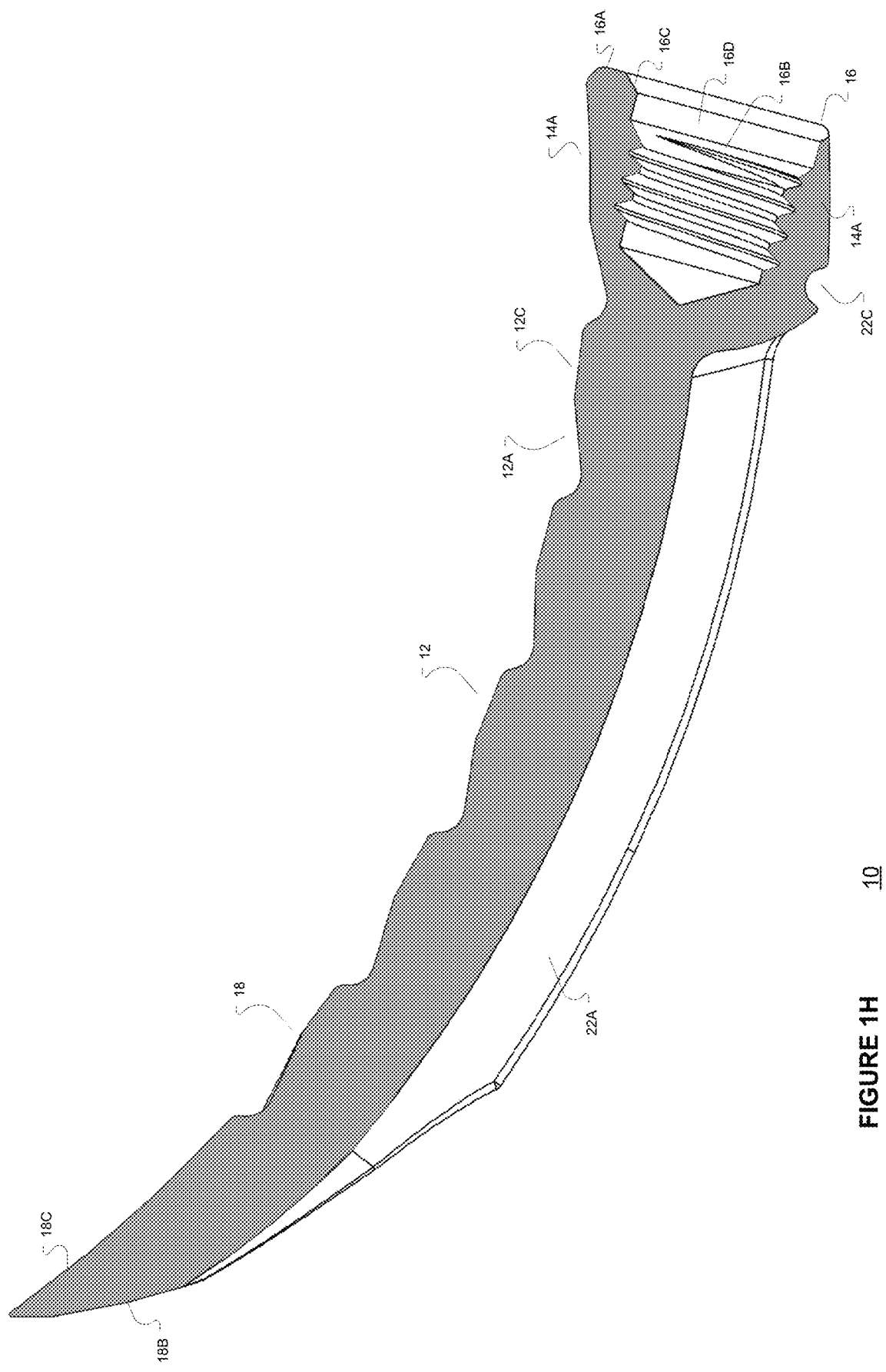
FIG. 1H is a cross sectional view of left side of an MBA taken at line BB shown in FIG. 1G according to various embodiments.
Figure 6B:
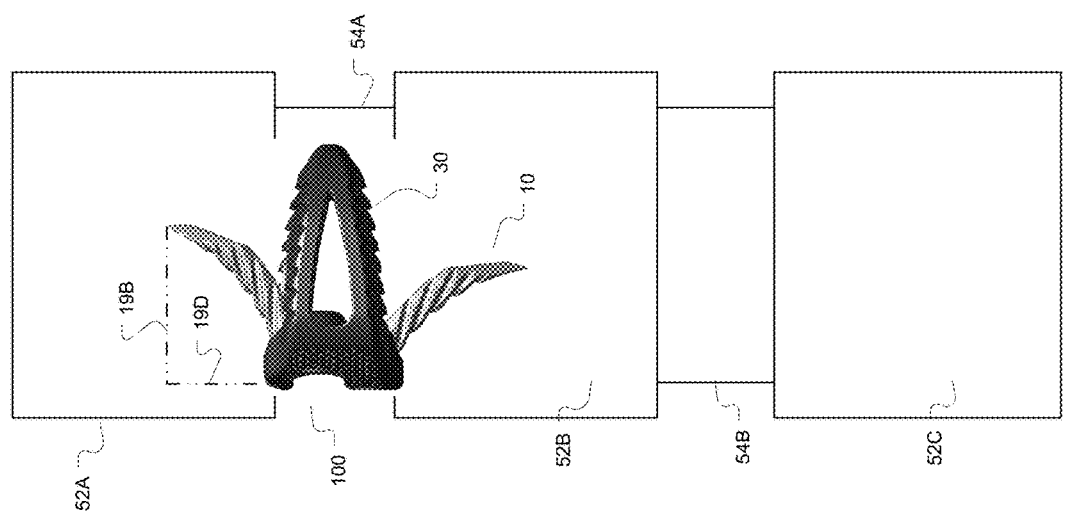
FIG. 6B is a left side view of an adjacent mammalian bony segments fixation system including an implant and a plurality of mammalian bony anchors operatively inserted between a center bony segment and an adjacent upper bony segment according to various embodiments.
Figure 6A:
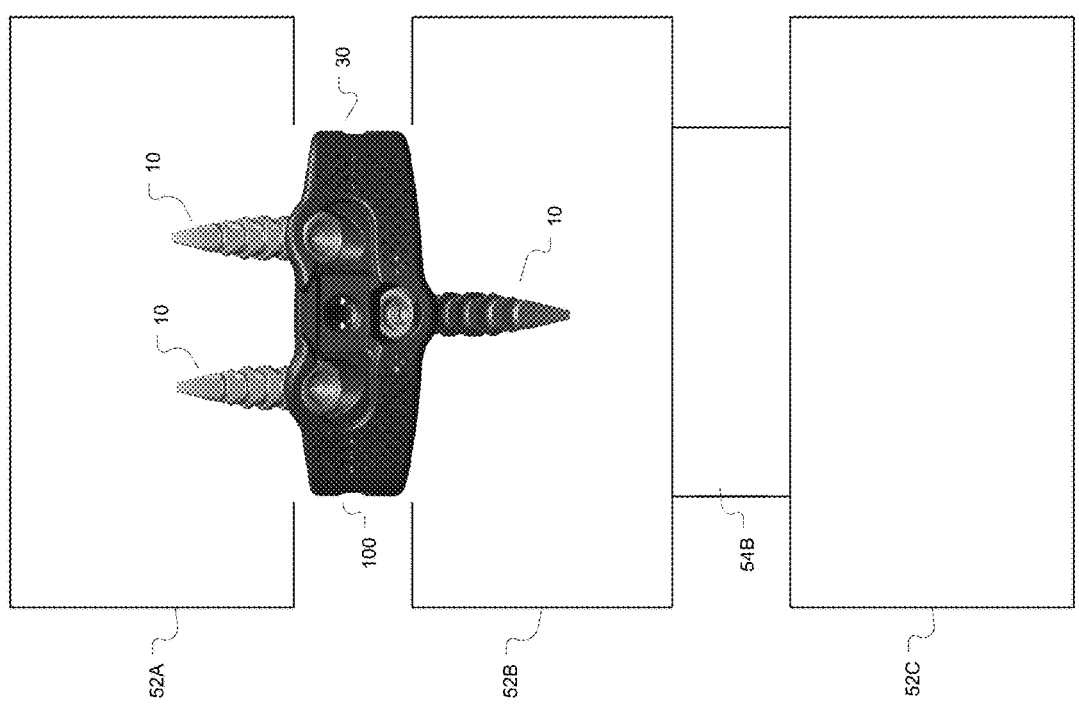
FIG. 6A is a posterior view of an adjacent mammalian bony segments fixation system including an implant and a plurality of mammalian bony anchors operatively inserted between a center bony segment and an adjacent upper bony segment according to various embodiments.

It may be desirable to treat one or more bony segments 52A-C via mammalian bony anchor(s) 10 such as in conjunction with other system(s) 30 to encourage bony fusion, stabilize, maintain spacing between, or couple the bony segments 52A-C (FIGS. 6A-6B). FIG. 1A is a simplified isometric front drawing of a mammalian bony anchor 10 according to various embodiments. FIG. 1B is a simplified isometric rear drawing of the mammalian bony anchor 10 according to various embodiments. FIG. 1C is a simplified top view of the mammalian bony anchor 10 according to various embodiments. FIG. 1D is a simplified bottom view of the mammalian bony anchor 10 according to various embodiments. FIG. 1E is a simplified left side view of the mammalian bony anchor 10 according to various embodiments. FIG. 1F is a simplified bottom front view of the mammalian bony anchor according to various embodiments. FIG. 1G is a simplified rear view of the mammalian bony anchor 10 according to various embodiments. FIG. 1H is a cross sectional view of left side of a mammalian bony anchor taken at line BB shown in FIG. 1G according to various embodiments.

As shown in FIGS. 1A-1H, the mammalian bony anchor (MBA) 10 includes a shaft 12, a base section 14, a tool interface 16, and a tapered extended tip section 18. As shown in FIGS. 1E and 1H, the MBA 10 may have an arcuate shape with a primary radius 17A for the base section 12, a first, secondary radius 17B for the tip section 18 where the radius 17A is larger than the radius 17B, and a third, tertiary radius 17D for the tip edge 18C. In an embodiment, the radius 17A may be about 1.5 to 2.5 times larger than radius 17B and about 1.75 to 2.0 times larger in an embodiment, 2.0 to 3.0 times larger than radius 17D. As shown in FIGS. 1E and 6B, the MBA 10 may have an effective depth of insertion 19B which is less than the overall length 17C the MBA 10. The MBA 10 may also have a height 19D where the length of the effective hypotenuse formed by 19B and 19D (square root of the sum of the squares of the 19B and 19D) is less than the overall length 17C of the BMA 10.

As shown in FIGS. 1A-1G, the shaft section 12 and tip section 18 may include a plurality of shelves or scallops 12A. Each scallop 12A may include a flat ledge 12C and an undercut 12B. The flat ledge 12C may ease insertion of the MBA 10 into a bony segment 52A-C while the remainder of each scallop 12A including the edge around the undercut 12B may help prevent expulsion of the MBA 10 once inserted into a desired position in a bony segment 52A-C.

As also shown in FIGS. 1A-1G, the tip section 18 may also include a large flat region 18C on the top, flat portions 18A on the sides, and a smaller flat region 18B on the bottom that may also ease insertion of the MBA 10 into a bony segment 52A-C. As also shown in FIGS. 1A-1G, the tip section 18 may have a narrower tip where the sides 18A may form an angle (19C in FIG. 1C) of about 20 to 60 degrees and about 40 degrees in an embodiment. As also shown in FIGS. 1A-1G, the bottom 22 of the MBA 10 may be partially cylindrical in relief, with smaller sections 22B in the tip section 18 than the sections 22A of the rear in the shaft section 12. The shape of the rear 22 may also reduce the force required to inset the MBA 10 into a desired position in a bony segment 52A-C.

Figure 2:
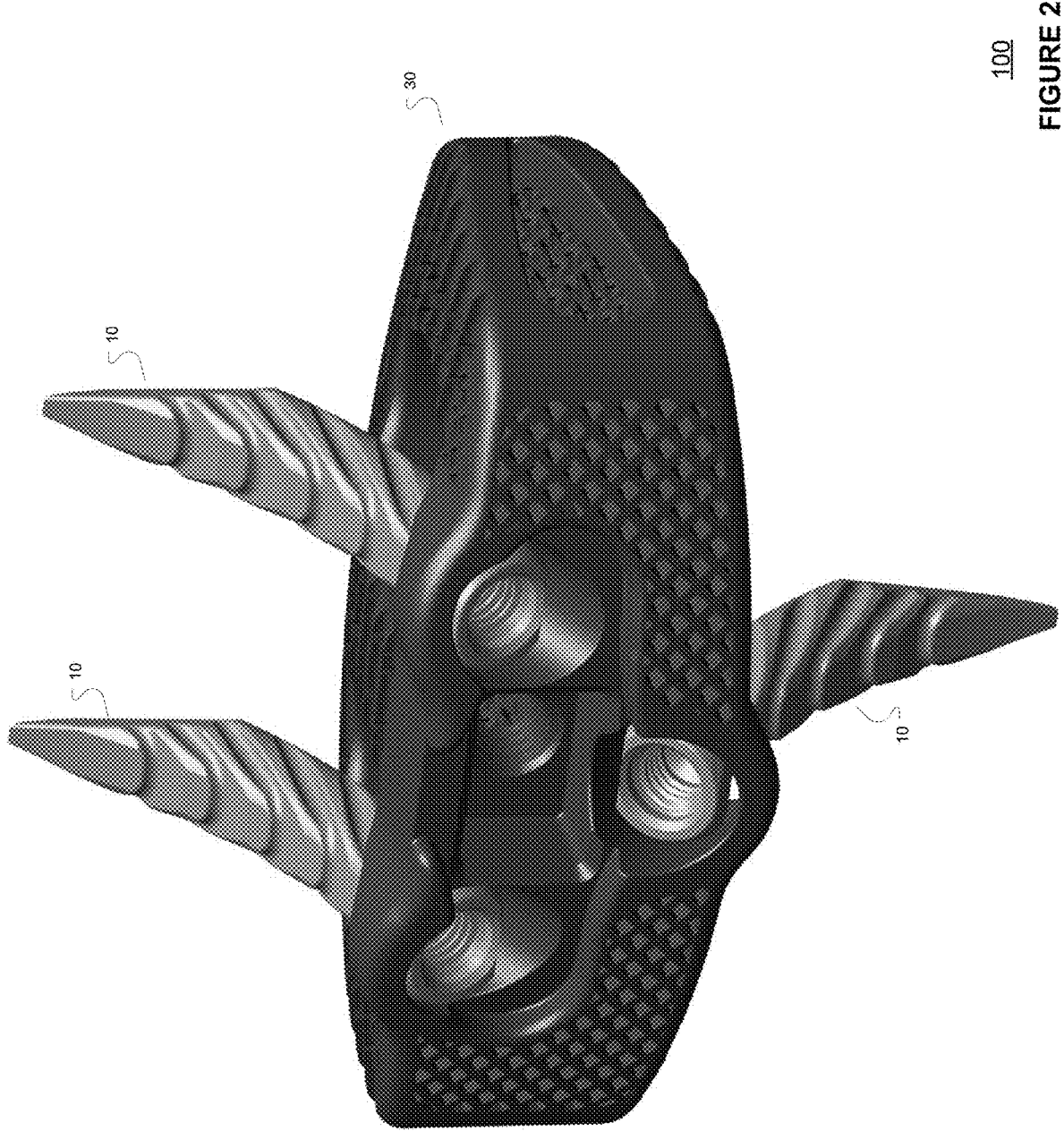
FIG. 2 is a simplified isometric view of an adjacent mammalian bony segments fixation system including an implant and a plurality of mammalian bony anchors according to various embodiments.
Figure 3A:
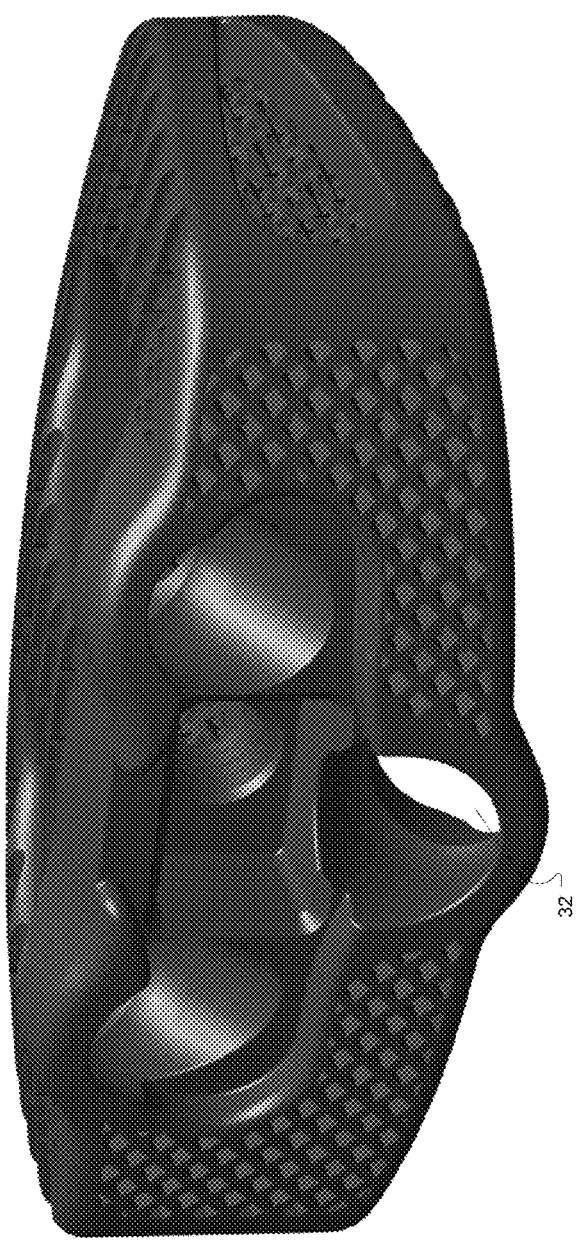
FIG. 3A is a simplified isometric front drawing of an adjacent mammalian bony segments implant according to various embodiments.
Figure 3B:
FIG. 3B is a simplified front drawing of an adjacent mammalian bony segments implant according to various embodiments.
Figure 3C:
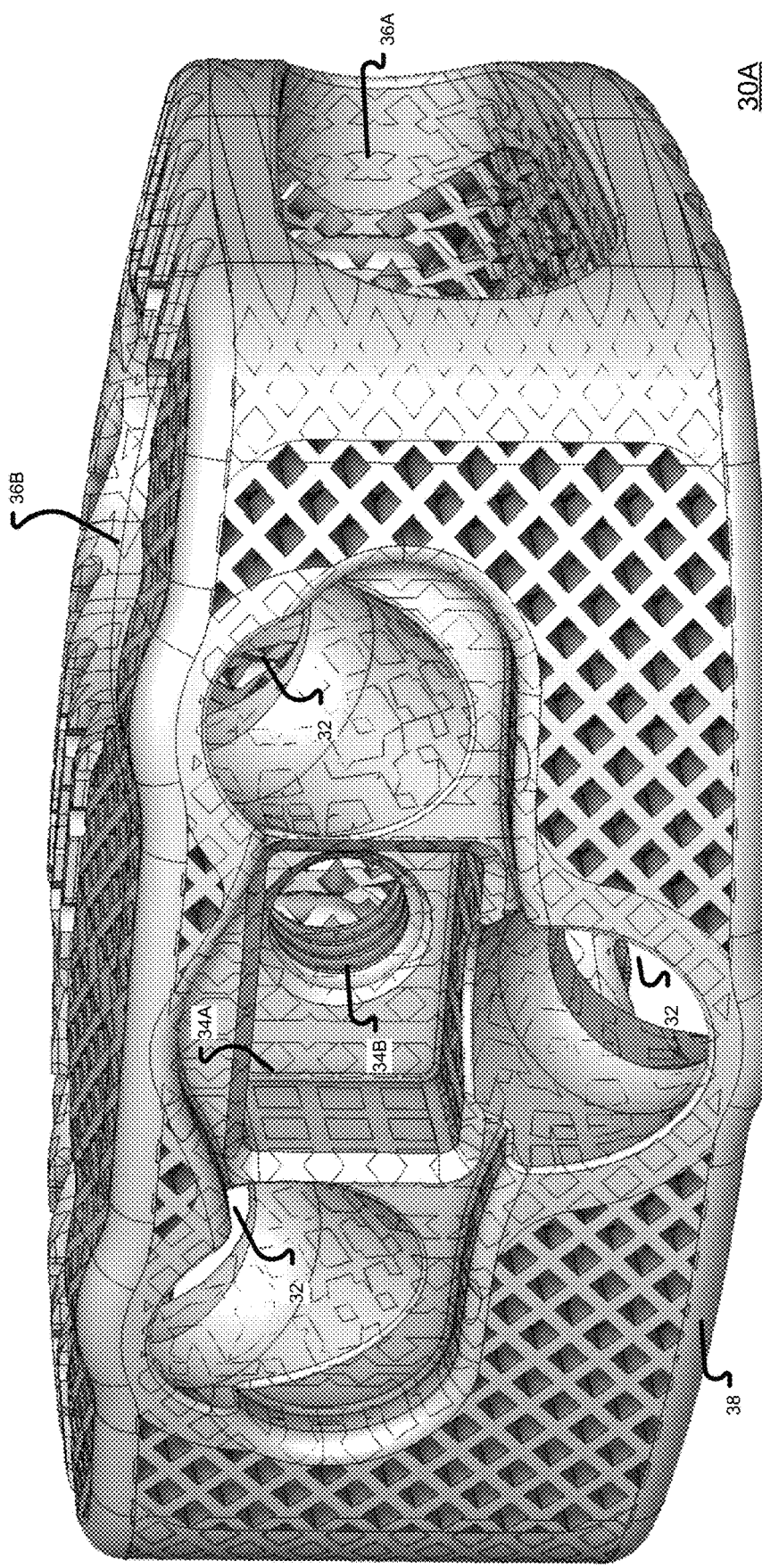
FIG. 3C is a simplified isometric front drawing of another adjacent mammalian bony segments implant according to various embodiments.
Figure 4:
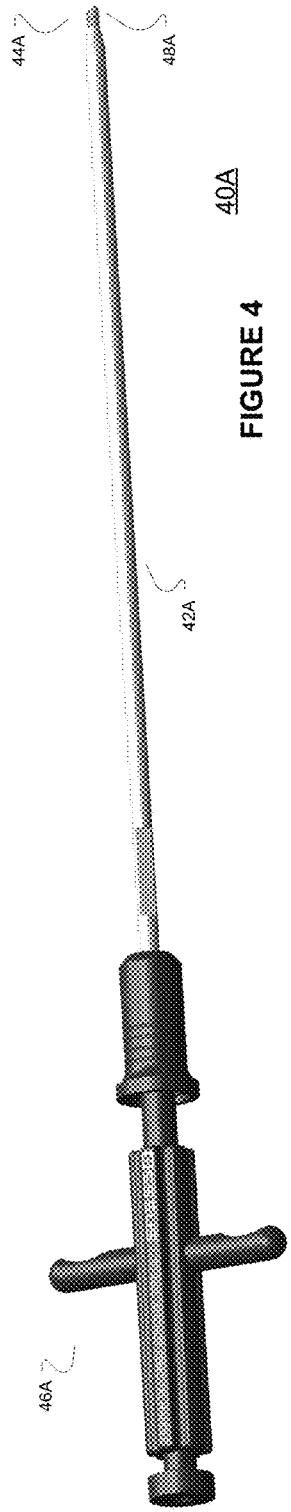
FIG. 4 is a simplified side view of straight-line removal tool for a curved MBA according to various embodiments.
Figure 5A:
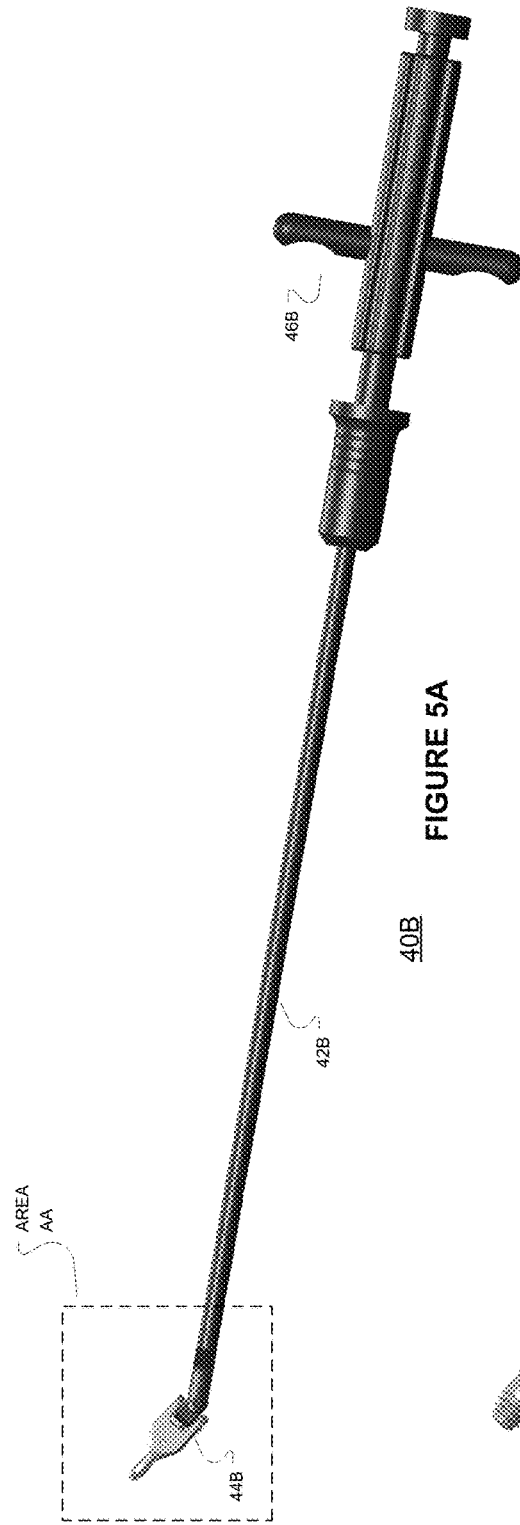
FIG. 5A is a simplified side view of variable-angle removal tool for a curved MBA according to various embodiments.
Figure 5B:
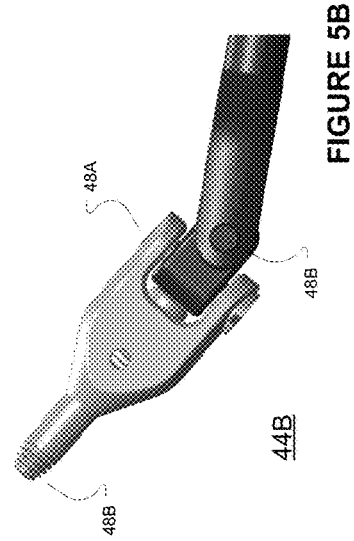
FIG. 5B is a simplified enlarged view of area AA of the variable-angle removal tool for a curved MBA shown in FIG. 5A.

In an embodiment, an MBA 10 may be inserted into a desired position in a bony segment 52A-C via an impaction tool that acts on the tool interface 16 flat impact surface 16A due to its configuration/geometry. As shown FIGS. 1A-1G, the tool interface 16 may include an internal threaded section 16B sized to receive a removal tool interface's external thread 48A, 48B as shown in FIGS. 4-5B. The tool interface 16 may also include a chamfer 16C and counterbore 16D each having a diameter greater than the internal threads 16B. The base 14 may have a flat top and bottom section 14A and partially spherical sides 14B. This base 14 configuration enables the MBA 10 to have a large range of pivotability when used in conjunction with an implant 30 such as shown in FIGS. 2-3B. As shown in FIGS. 3A-3C, an implant 30, 30A may include a plurality of bone anchor interfaces 32 that are spherical in relief and enable the MBA 10 base 14 section to pivot over a large range. As shown in FIG. 3C, 8L, 8S, and others, the implant 30A may include a tool interface relief 34A, a tool interface internally thread bore 34B, a side fenestration 36A, and a top to bottom fenestration 36B where the fenestrations 36A, 36B may be packed or filled with an osteoconductive material prior to the implant 30, 30A implantation between two, adjacent bony elements.

As shown in FIG. 2, when coupled to an implant, an MBA 10 may form about a 90-degree angle at its tip section 18 relative to the implant 30. When inserted between bony sections 52A-52B as shown in FIGS. 6A and 6B, the MBA 10 may provide substantial retention and anti-expulsion force with the bony segments 52A-B. In an embodiment, the bony segments 52A-C may be vertebrae with disc nucleus 54A-B located between adjacent vertebrae 52A, 52B or 52B, 52C. In an embodiment, the vertebrae 52A-C may be lumbar vertebrae and an adjacent mammalian bony segments fixation system (AMBSFS) 100 may be ideally inserted between two, adjacent vertebrae 52A-C as shown in FIGS. 6A-6B.

In an embodiment, an AMBSFS 100 may include an implant 30 and a plurality of MBA (anchors) 10. As shown in FIGS. 6A and 6B, two MBA 10 may engage or affixed to an upper bony segment 52A and one MBA 10 may engage or affixed to a lower, adjacent bony segment 52B for the implant 30. As described with reference to FIGS. 7A-9F, in an embodiment, a combination implant and anchor inserter (CIAIS) 120 may be employed by a user (such as a surgeon) to implant a AMBSFS between two, adjacent bony constructs (as shown in FIG. 6C). In an embodiment, the CIAIS 120 may store three MBA 10 of a AMBSFS 100 in an implant and anchor insertion head (IAIH) 80 while simultaneously holding/coupled to the AMBSFS implant 30. The CIAIS 120 may further enable a User to first fixably place the implant 30 between adjacent bony segments (ABS) 52A, 52B including from an anterior position (part an anterior lumbar interior fusion (ALIF)). The CIAIS 120 may second enable the User to fixably insert one or more MBA 10 through the implant 30 into one of the ABS 52A, 52B while the CIAIS 120 remains in the same location (adjacent the ABS 52A, 52B).

FIG. 7A is an isometric simplified drawing of a combination implant and anchor inserter system (CIAIS) 120 according to various embodiments. FIG. 7B is an isometric simplified drawing of the operational elements of the CIAIS 120 as shown in FIG. 7A according to various embodiments. As shown in FIGS. 7A-7B, a CIAIS may include a combination Implant and anchor inserter (CIAI) 60, several anchor impact elements (AIE) 70, a Torque limited ratchet (TLR) 90, and a Coupler 110 between TLR 90 and CIAI 60. As also shown in FIGS. 7A-7B, a CIAI 60 may include a user grip section 62, an implant and anchor insertion head (IAIH) 80, and a shaft 64 between the user grip section 62 and the IAIH 80.

As also shown in FIGS. 7A-7B, a TLR 90 may include a handle 92 and a tool interface 94. In an embodiment, the TLR 90 may be configured to enable a predetermined maximum torque to be applied to a tool coupled to the interface 94. As shown in FIG. 7B, the tool coupler 110 may include a TLR 90 interface 112, a CIAI 60 implant connection system (ICS) 88 interface 114, and user grip 116. In an embodiment, the TLR 90 interface 112 may be sized and shaped to interface with TLR 90 interface 94. The tool coupler 110 CIAI 60 ICS 88 interface 114 may be sized and shaped to interface with the CIAI 60 ICS 88 tool interface 88A. In an embodiment, the tool coupler 110 may also be torque limiting via the user grip 116.

In an embodiment, the anchor impact elements (AIE) 70 may include a head 72, shaft 76, and distal end 74. The head 72 has a flat proximal surface that may be impacted by an impact tool such as a hammer. The distal end 74 may be shaped to pass through segments 82E, 82F of the IAIH 80 to engage and drive an MBA 10 stored in the IAIH 80. The shaft 76 may also be shaped to pass through segment 82E but not 82F of the IAIH 80—limiting the overall passage of the distal end 74 within the IAIH 80 in an embodiment. The shaft 76 and distal end 74 may also be shaped to pass through CIAI user grip 60 ports 62A as shown in FIG. 7A and FIG. 8E.

Figure 8A:
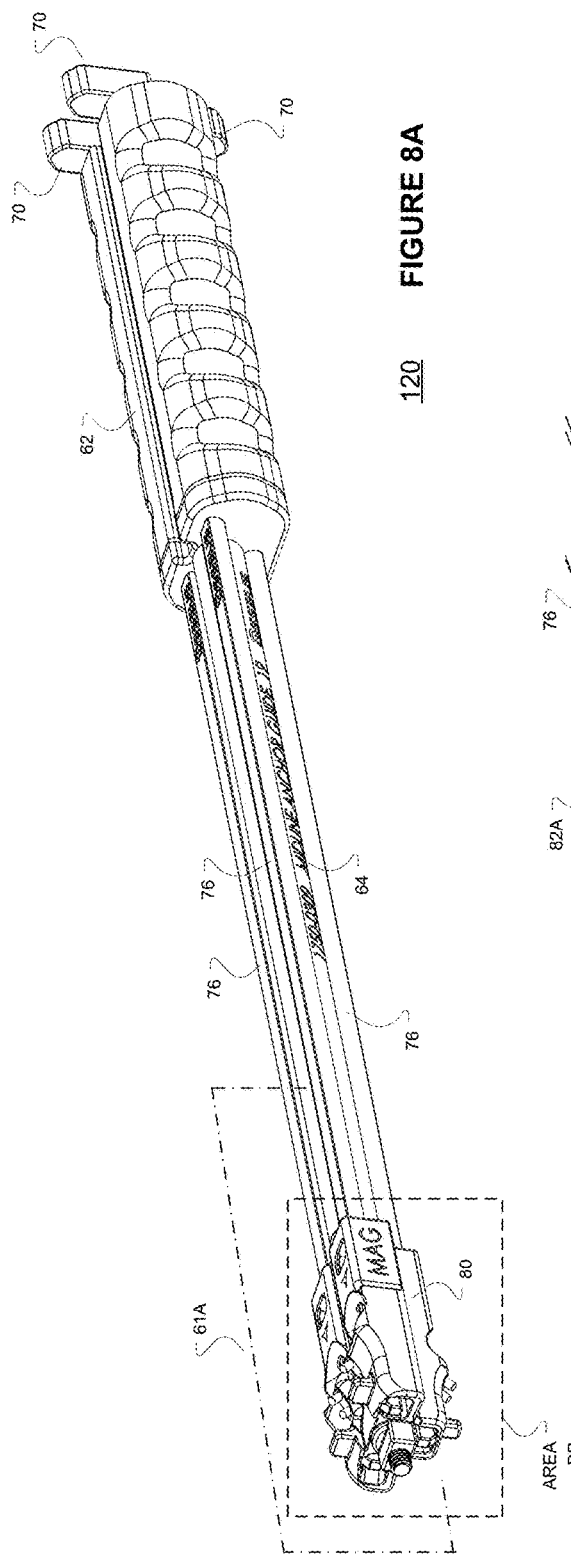
FIG. 8A is an isometric simplified drawing of a combination implant and anchor inserter (CIAI) and implant elements according to various embodiments.

FIG. 8A is an isometric simplified drawing of a combination Implant and anchor inserter system (CIAIS) 120 according to various embodiments. As shown in FIG. 8A, the CIAIS 120 includes a CIAI 60 and three AIE 70. The AIE 70 are shown fully inserted into the IAIH (head) 80 via the CIAI user grip 62. As shown in FIG. 8A, AIE 70 shafts 76 are parallel and adjacent to the CIAI shaft 64 that couples the grip 62 to the implant and anchor insertion head (IAIH) 80.

Figure 8B:
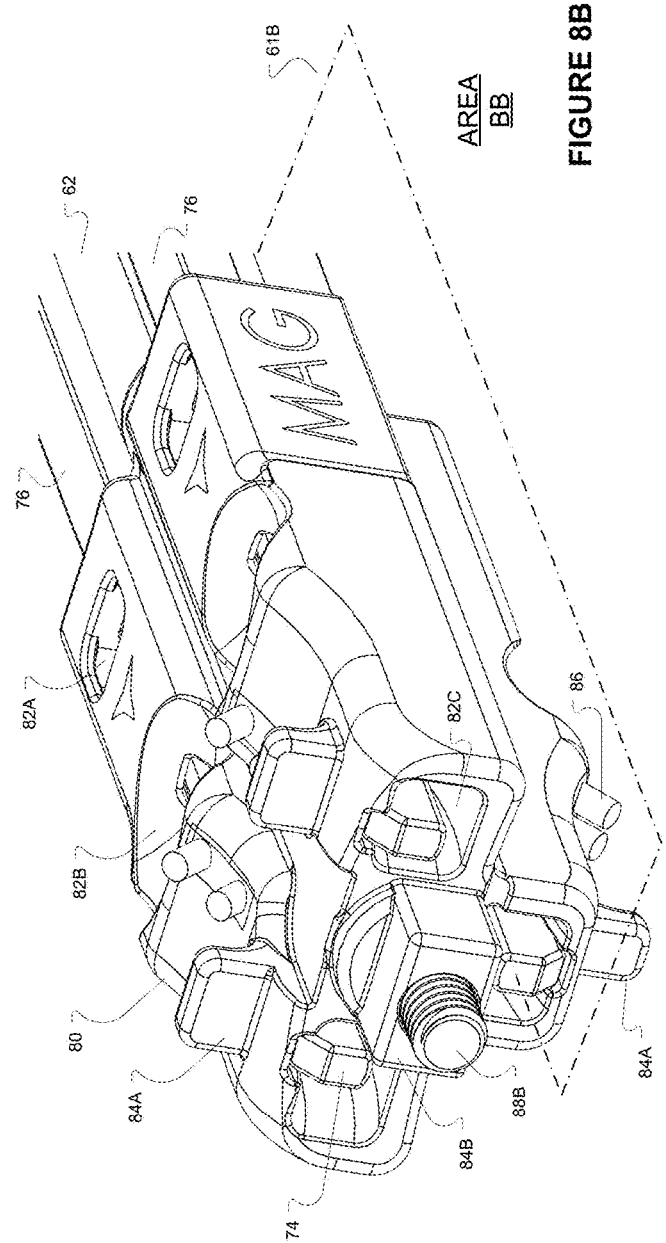
FIG. 8B is an isometric simplified drawing of area BB of the combination implant and anchor inserter (CIAI) as shown in FIG. 8A according to various embodiments.

FIG. 8B is an isometric simplified drawing of area BB of the combination Implant and anchor inserter system (CIAIS) 120, in particular the IAIH 80 as shown in FIG. 8A according to various embodiments. In an embodiment, the IAIH 80 may be able to load, store, and enable a user to implant three MBA 10 and couple and enable a user to insert an implant 30. As shown in FIG. 8B, a IAIH 80 may include ports 82B sized to enable an MBA 10 to be inserted therein. The IAIH 80 may also include two anchor retention systems (ARS) 86 per port 82B. The ARS 86 are configured to engage an MBA 10 base 14 so a User may insert an MBA 10 within a port 82B with tactile verification while holding an MBA 10 within the IAIH 80 unless ejected from the port 82C. The IAIH 80 may also include a visualization and cleaning port 82A that allows a User to visualize the position of AIE 70 distal 74 and shaft 76 in an embodiment. Further, a IAIH 80 may include MBA 10 ejection or implantation ports 82C. In an embodiment the ports 82C are configured to align with implant's 30 MBA anchor interfaces 32 when the implant 30 is coupled to the IAIH 80.

As also in FIG. 8B, a IAIH 80 may include elements 84A, 84B, 88B that enable an implant 30 to be securely coupled to the IAIH 80 during implantation into a AMBSFS 100 and then be disconnected therefrom. In an embodiment, the IAIH 80 includes three implant 30 support tabs 84A that seat against the implant 30 rear area or section 38. The IAIH 80 may also include a implant 30 recess engagement protrusion 84B that is sized and shaped to fit securely and removably within the implant 30, 30A tool interface relief 34A as shown in FIG. 3C. The IAIH 80 may further include an implant connection system ICS 88 with a threaded implant 30 interface 88B that is configured to be threadably secured and removed with the implant 30 tool interface internally thread bore 34B as shown in FIG. 3C. The combination of the support tabs 84A, recess engagement protrusion 84B, and threaded implant 30 interface 88B, enable a User to securely couple an implant the CIAI 60 IAIH 80 and securely insert the implant 30 between adjacent bony elements 52A, 52B.

FIG. 8C is a simplified exploded side view of a combination implant and anchor inserter (CIAI) 60 shown in FIG. 8A according to various embodiments. As shown in FIG. 8C, the CIAI 60 may include a user grip 62, shaft 64, IAIH 80, six ARS 86, and ICS 88. Each ARS 86 may include ends 86A connected together by a deflectable wire 86B. In an embodiment, the wire 86B may be a restorably, deflectable wire including Nitinol wire. As noted, each ARS 86 may be shaped and sized to deflectably engage an MBA 10 head. The ICS 88 may include a tool interface 88A, implant 30 bore 34B bore-interface 88B, and elongated circular shaft 88C. As shown in FIG. 8C, the elongated circular shaft 88C may have a larger diameter on its proximal end by interface 88A versus the diameter at the distal end by the interface 88B. The shaft 64 may include a port 64B that is sized to enable the ICS 80 distal end 88C to rotate therein as shown in FIG. 8F. The grip 62 may include a port 62B may is sized to enable the ICS 80 proximal end 88C to rotate therein as shown in FIG. 8E.

Figure 8G:
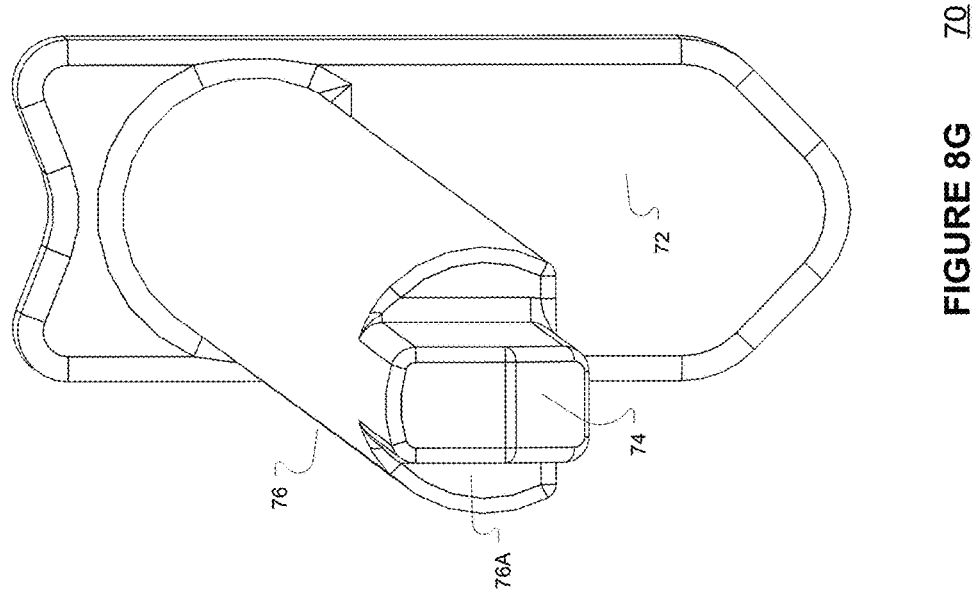
FIG. 8G is a front simplified drawing of an anchor impact element (AIE) of a CIAIS shown in FIG. 7B according to various embodiments.
Figure 8E:
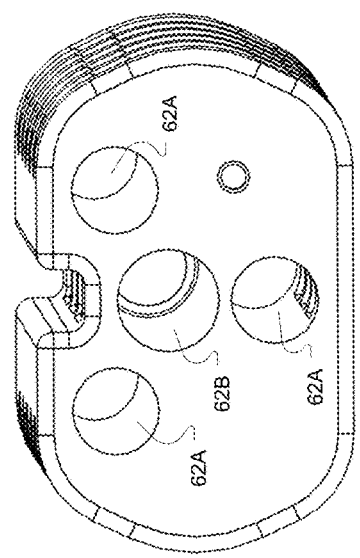
FIG. 8E is a front simplified drawing of user grip section of a combination implant and anchor inserter (CIAI) shown in FIG. 8A according to various embodiments.
Figure 8F:
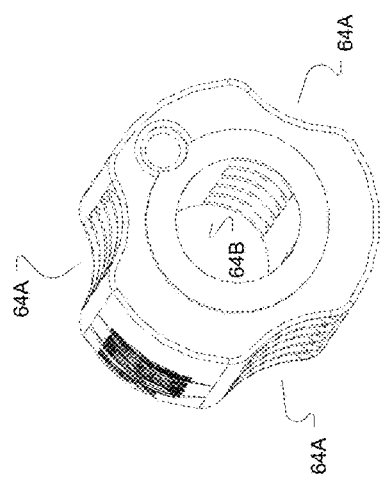
FIG. 8F is a front simplified drawing of a shaft between the user grip section and implant and anchor insertion head (IAIH) of a combination implant and anchor inserter (CIAI) shown in FIG. 8A according to various embodiments.

FIG. 8D is a simplified drawing of area CC and FIG. 8G is a front simplified drawing of an anchor impact element (AIE) 70 distal end 74 of a CIAIS 120 shown in FIG. 7B according to various embodiments. As shown in FIGS. 8D and 8G, the AIE 70 may a transition from its proximal shaft section 76 to its distal shaft section 74 where the section 76 has a larger envelope or cross-sectional area than section 74. At the intersection between section 76 and section 74, inserts 76A may be present. As discussed above, the IAIH may have ports and sections 82G, 82E, and 82F that are sized to enable the section 74 to extend into the IAIH 60 and impact-advance an MBA stored therein while limiting the travel of the AIE 70 with the IAIH 60. The large flat area 72 is shaped to enable a User to strike or impact the AIE 70 thereby (such as via a hammer or mallet) to advance the AIE 70 and an associated MBA 10 in an embodiment.

As shown in FIGS. 8D and 8G, the AIE 70 distal section 74 may be rectangular in cross-section 74A with a flat, upper distal end portion 74B and a slanted inward lower distal end portion 74C. As discussed in more detail, the flat, upper distal end portion 74B may initial engage-impact-advance an MBA 10. As the AIE is advanced into the IAIH 60, the slanted inward lower distal end portion 74C may engage-impact-advance an MBA 10 due the shape of its path in the IAIH 60 and the accurate shape of the MBA 10. In an embodiment, the upper section 74B and lower section 74C may be evenly split along the distal end. The lower section 74C may slanted about 45 degrees inward in an embodiment.

FIG. 8E is a front simplified drawing of a user grip section 62 of a combination implant and anchor inserter (CIAI) 60 shown in FIG. 8A according to various embodiments. As shown in FIG. 8E, the grip section 62 includes ports 62A that are sized to enable an AIE 70 proximal section 76 to pass therethrough. The grip section 62 also includes port 62B that is sized to enable the ICS 88 proximal shaft section 88C to pass therethrough.

FIG. 8F is a front simplified drawing of a shaft 64 between the user grip section 62 and implant and anchor insertion head (IAIH) 80 of a combination implant and anchor inserter (CIAI) 60 shown in FIG. 8A according to various embodiments. As shown in FIG. 8F, the shaft section 64 includes reliefs 64A that are shaped to enable an AIE 70 proximal section 76 to pass thereby. The shaft section 64 also includes port 64B that is sized to enable the ICS 88 distal shaft section 88C to pass therethrough.

Figure 8H:
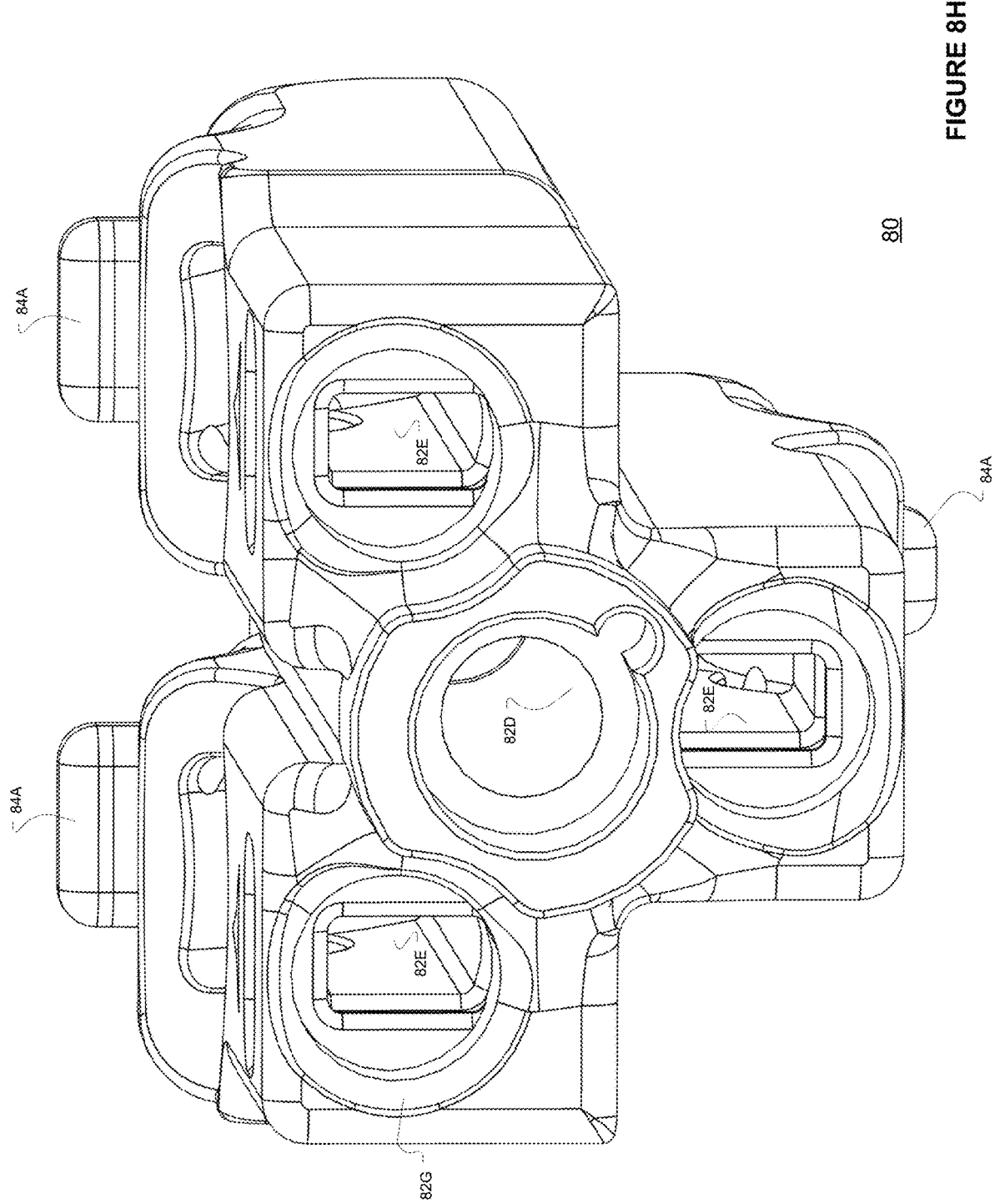
FIG. 8H is a rear simplified drawing of an implant and anchor insertion head (IAIH) of a combination implant and anchor inserter (CIAI) shown in FIG. 8A according to various embodiments.
Figure 8J:
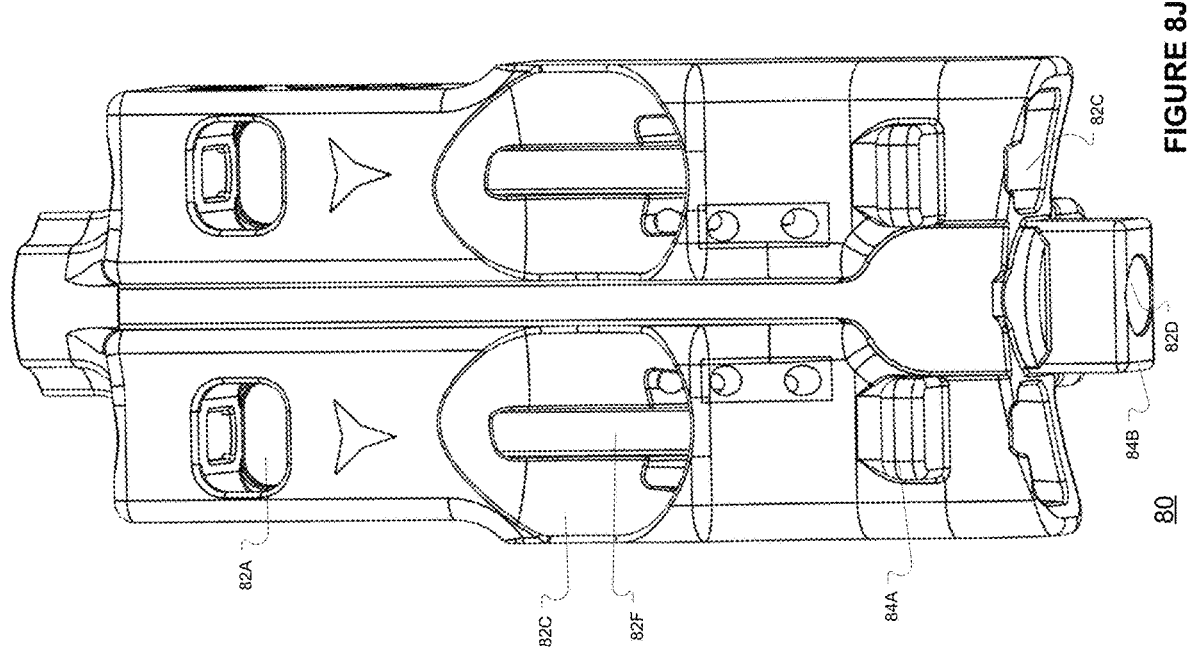
FIG. 8J is a top simplified drawing of an implant and anchor insertion head (IAIH) of a combination implant and anchor inserter (CIAI) according to various embodiments.
Figure 8I:
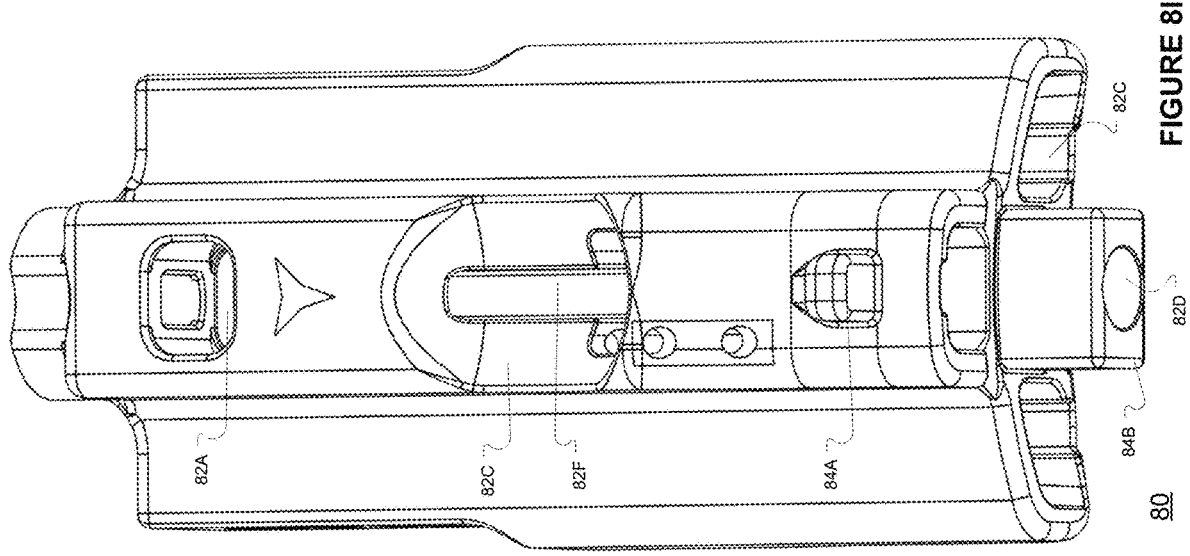
FIG. 8I is a bottom simplified drawing of an implant and anchor insertion head (IAIH) of a combination implant and anchor inserter (CIAI) according to various embodiments.

FIG. 8H is a rear simplified drawing, FIG. 8I is a bottom simplified drawing, and FIG. 8J is a top simplified drawing of an implant and anchor insertion head (IAIH) 80 of a combination implant and anchor inserter (CIAI) 60 shown in FIG. 8A according to various embodiments. As shown in FIG. 8H, IAIH 80 includes three relief sections 82G sized to allow the AIE 70 shaft section 76 to mate therein. IAIH 80 further includes three ports 82E sized to allow the AIE 70 distal shaft section 74 to pass therethrough.

As shown in FIGS. 8I and 8J, the IAIH 80 may include one MBA port 82C and AIE 70 port 82E on its bottom and two MBA port 82C and AIE 70 port 82E on its top. As also shown in FIGS. 8I and 8J, the MBA ports 82C may include reliefs 82F that are shaped to enable the AIE 70 distal section 74 to pass therethrough so the AIE 70 distal section 74 ends 74B, 74C may engage-impact-advance an MBA 10 stored therein.

Figure 8K:
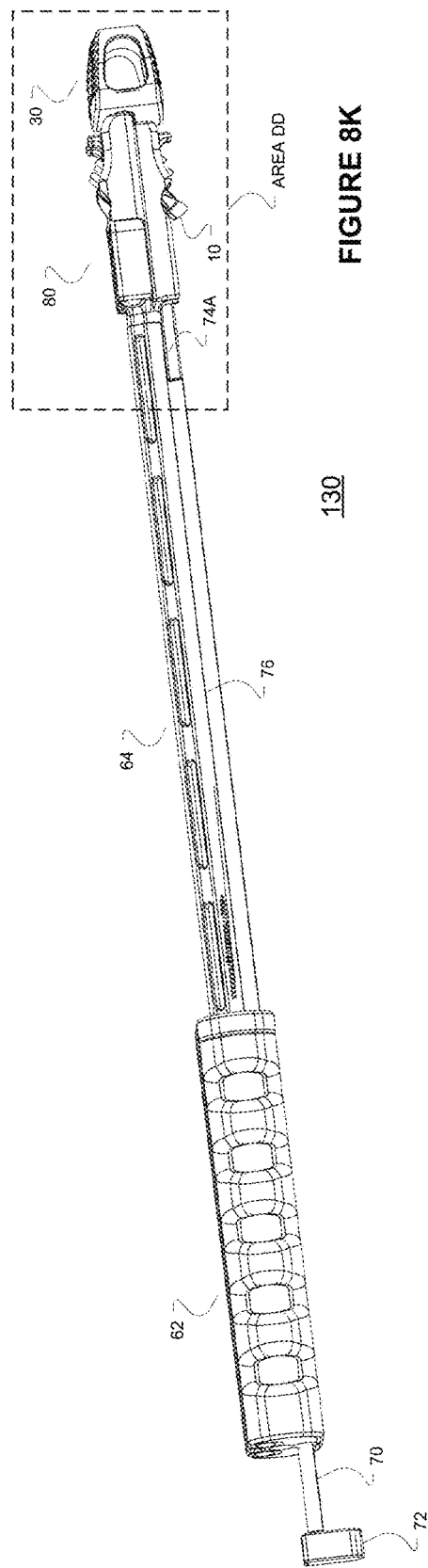
FIG. 8K is an isometric side simplified drawing of a combination implant and anchor inserter (CIAI) coupled to an implant and mammalian bony anchors with an anchor impact element (AIE) withdrawn proximally according to various embodiments.
Figure 8L:
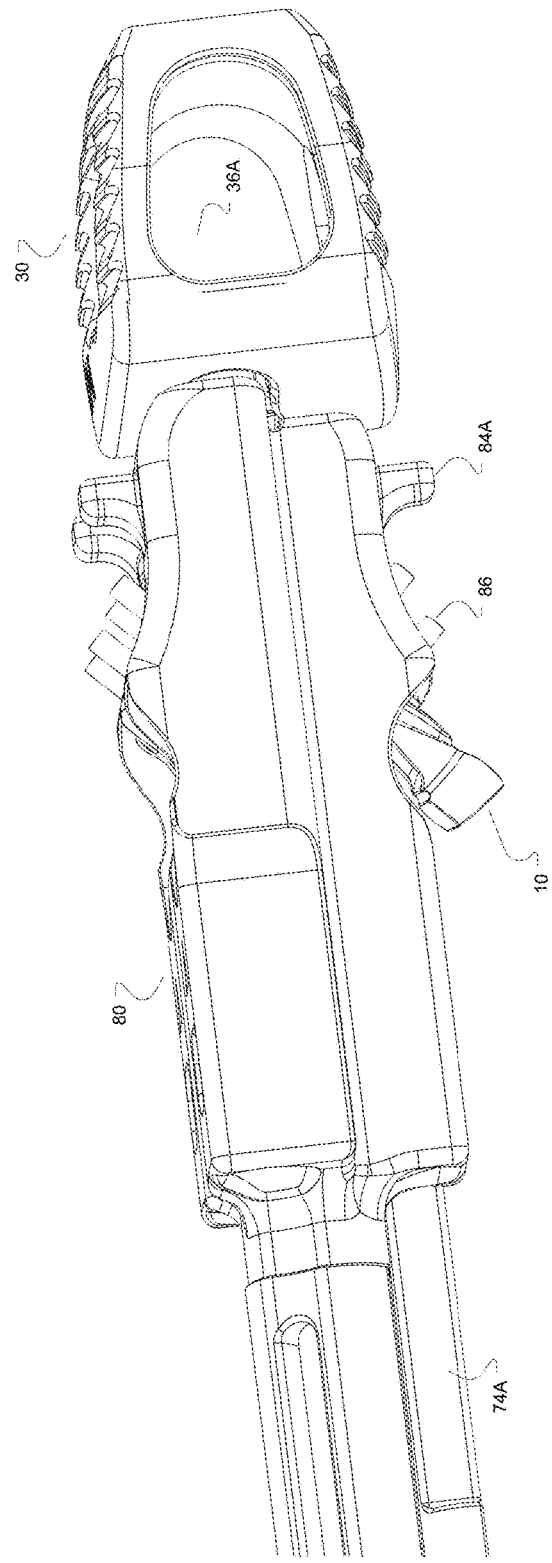
FIG. 8L is an isometric side simplified drawing of area DD of a combination implant and anchor inserter (CIAI) coupled to an implant and a mammalian bony anchor with an anchor impact element withdrawn proximally according to various embodiments.

FIG. 8K is an isometric side simplified drawing, FIG. 8L is an isometric side simplified drawing of area DD (shown in FIG. 8K), and FIG. 8M is a cross section drawing along plane 61A shown on FIG. 8A of area DD of a combination implant and anchor inserter system CIAIS 120 coupled to an implant 30 and an MBA 10 beginning to be inserted into a IAIH 80 since the AIE 70 is at least partially withdrawn proximally according to various embodiments. As shown in FIGS. 8L and 8M, the AIE 70 distal section 74 (such as slanted end section 74C) is withdrawn a distance sufficient to enable an MBA 10 to be inserted in an IAIH 80 anchor insertion port 82B.

FIG. 8N is a cross section drawing along plane 61A shown on FIG. 8A of area DD of a combination implant and anchor inserter (CIAIS) 120 coupled to an implant 30 and an MBA 10 that has been advanced-engaged by AIR 70 distal section 74 so the MBA 10 is extending partially into the implant 30. As shown in FIG. 8N, the AIE 70 distal flat end 74B may be engaging the MBA 10 base 14. As also shown in FIG. 8N, the AIE 70 distal section 74 is further extended into the IAIH 80.

FIG. 8O is a cross section drawing along plane 61A shown on FIG. 8A of area DD of a combination implant and anchor inserter (CIAIS) 120 coupled to an implant 30 and an MBA 10 that has been further advanced-engaged by AIR 70 distal section 74 so the MBA 10 is further extending partially into the implant 30. As shown in FIG. 8O, the AIE 70 distal slanted end 74C may be engaging the MBA 10 base 14. As also shown in FIG. 8O, the AIE 70 distal section 74 is further extended into the IAIH 80.

Figure 8Q:
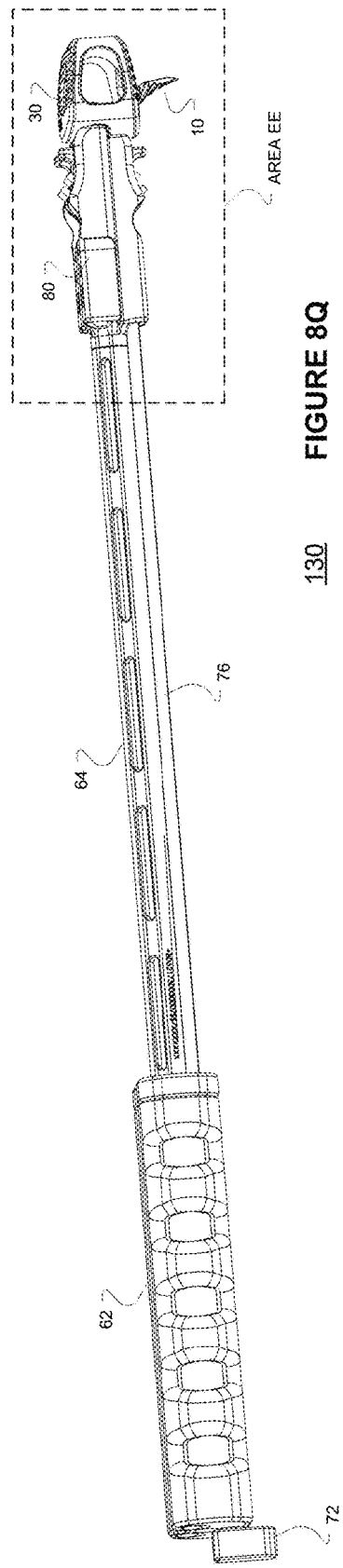
FIG. 8Q is an isometric side simplified drawing of a combination implant and anchor inserter (CIAI) coupled to an implant and a mammalian bony anchor fully extended therefrom and with an anchor impact element (AIE) forwarded completely distal according to various embodiments.
Figure 8R:
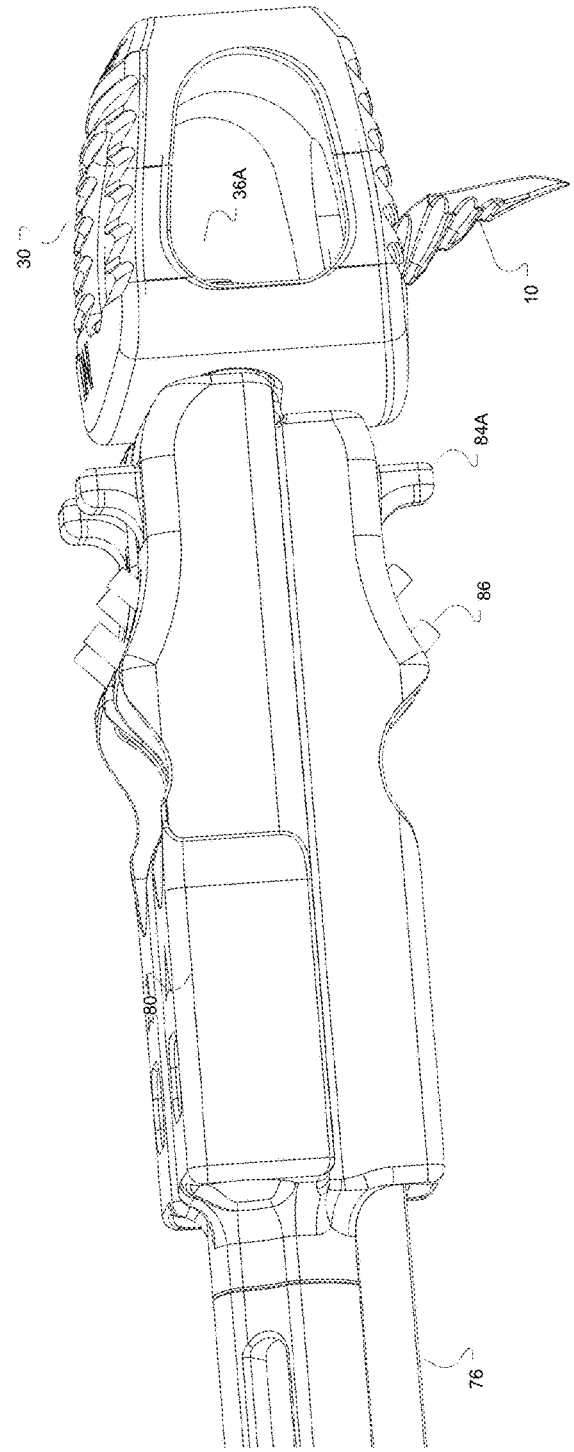
FIG. 8R is an isometric side simplified drawing of area EE of a combination implant and anchor inserter (CIAI) coupled to an implant and a mammalian bony anchor fully extended therefrom and with an anchor impact element (AIE) forwarded completely distal according to various embodiments.

FIG. 8Q is an isometric side simplified drawing and FIG. 8R is an isometric side simplified drawing of area EE of FIG. 8Q of a combination implant and anchor inserter (CIAIS) 120 coupled to an implant 30 and an MBA 10 that has been completed advanced-engaged by AIR 70 distal section 74 so the MBA 10 is fully inserted into and through the implant 30. As shown in FIGS. 8Q and 8R, the AIE 70 flat end 72 has been advanced to abut against the CIAI 60 user grip 62. As also shown in FIG. 8P, the AIE 70 distal section 74 is further extended into the IAIH 80.

FIG. 8S is a cross section drawing along plane 61B of area DD shown in FIG. 8A of a combination implant and anchor inserter (CIAIS) 120 coupled to an implant 30 and an MBA 10 that has been completed inserted into the IAIH 80 anchor port 82B. As shown in FIG. 8S, an MBA 10 head 14 may be engaged by ARS 86 once fully inserted. FIG. 8T is a cross section drawing along plane 61B of area DD shown in FIG. 8A of a combination implant and anchor inserter (CIAIS) 120 coupled to an implant 30 and an MBA 10 that has been completed inserted into and through an implant 30. FIGS. 8S and 8T further show the AIE distal section 74 pass-through sections 82E, 82F of the IAIH 80 of a CIAI 60 in an embodiment.

Via the CIASIS 120, an implant 30 and three MBA 10 may be inserted between two, adjacent bony segments such as shown in FIGS. 6A and 6B. FIG. 10 is an algorithm 140 for employing an CIASIS 120 to insert an AMBSFS including an implant 30 and three MBA 10 between ABS. FIGS. 9A-9G are simplified diagrams showing the activities of algorithm 140 for employing an CIASIS 120 to insert an AMBSFS including an implant 30 and three MBA 10 between ABS.

FIG. 9A is a side upside down drawing of a combination implant and anchor inserter system (CIAIS) 120 with a mammalian bony anchor 10 partially being inserted therein per activity 142 of algorithm 140. In an embodiment, all the MBA of a AMBSFS may be inserted into the CIAIS 120 IAIH 80. Then as shown in FIG. 9B, a TLR 90, coupler 110, and combination implant and anchor inserter (CIAI) 60 may be employed to couple the IAIH 80 to an implant 30 per activity 144 of algorithm 140 according to various embodiments. The TLR 90 may be operatively coupled to the ICS 88 via the coupler 110, so the ICS 88 implant interface 88B may securely couple with the implant 30 threaded bore 34B. Once secured, the TLR 90, and coupler 110 may be disconnected from the CIAI 60.

Then the combination implant and anchor inserter (CIAI) 60 coupled to an implant 30 with mammalian bony anchors 10 stored therein prior to implant insertion may be inserted between adjacent bony segments AMBSFS 100 as shown in FIG. 9C and algorithm 104 activity 146 according to various embodiments. In an embodiment, a hammer or mallet may be applied to the CIAI 60 user grip 62 proximal end to advance an insert between adjacent bony segments AMBSFS 100 as shown in FIG. 9D.

Also shown in FIG. 9D, the AIE 70 may be inserted into the ports 62A of CIAI 60 until the AIE 70 distal section 74 flat ends 74B engage the MBAs 10 stored in the IAIH 80 per activity 148 of algorithm 140. Then by advancing the AIE 70 flat section 72 to the CIAI 60 user grip 62 proximal end, the MBA 10 may be inserted through and to the implant 30 and into the adjacent bony segments 52A, 52B per activity 152 of algorithm 140. In an embodiment, a hammer or mallet may be applied to the AIEs 70 flat heads 72 to advance the MBAs 10 through and to the implant 30 and into the adjacent bony segments 52A, 52B as shown in FIG. 9E. In an embodiment, one or two MBA 10 may be inserted at a time by only advancing one or more AIE 70.

Figure 9F:
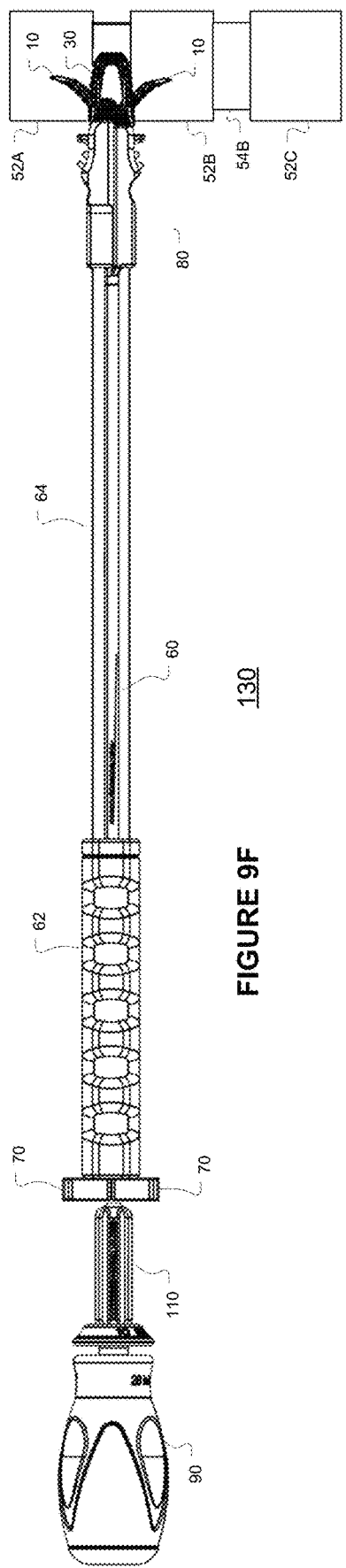
FIG. 9F is a side drawing of a TLR, coupler, and combination implant and anchor inserter (CIAI) being decoupled to an implant with mammalian bony anchors stored therein where the implant is fully inserted between adjacent bony segments according to various embodiments.
Figure 9G:
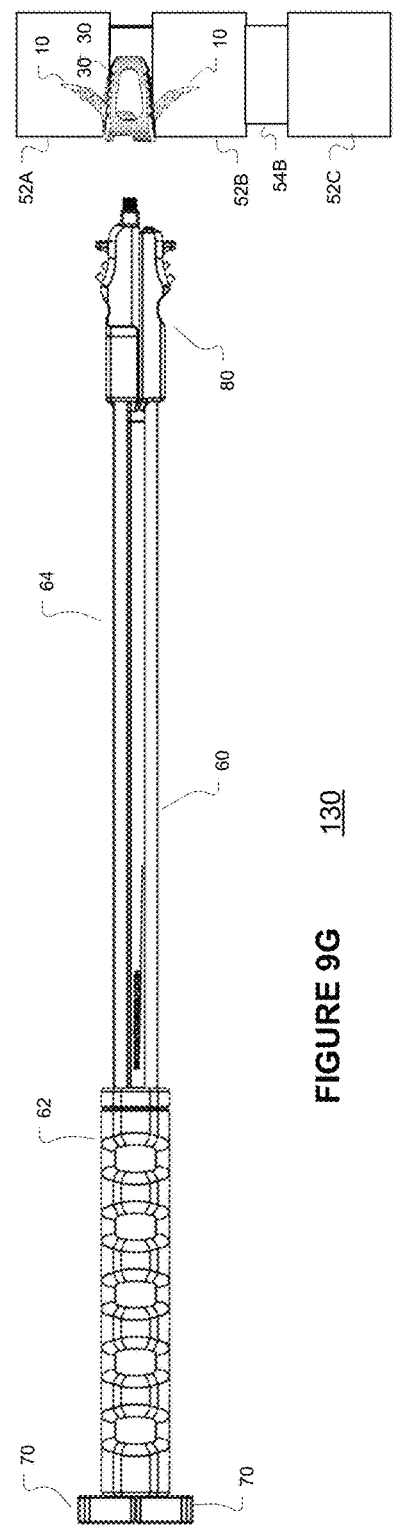
FIG. 9G is a side drawing of AIEs fully inserted and combination implant and anchor inserter (CIAI) disconnected from the implant where the mammalian bony anchors are fully implanted into adjacent bony segments and the implant fully inserted between adjacent bony segments according to various embodiments.
Figure 10:
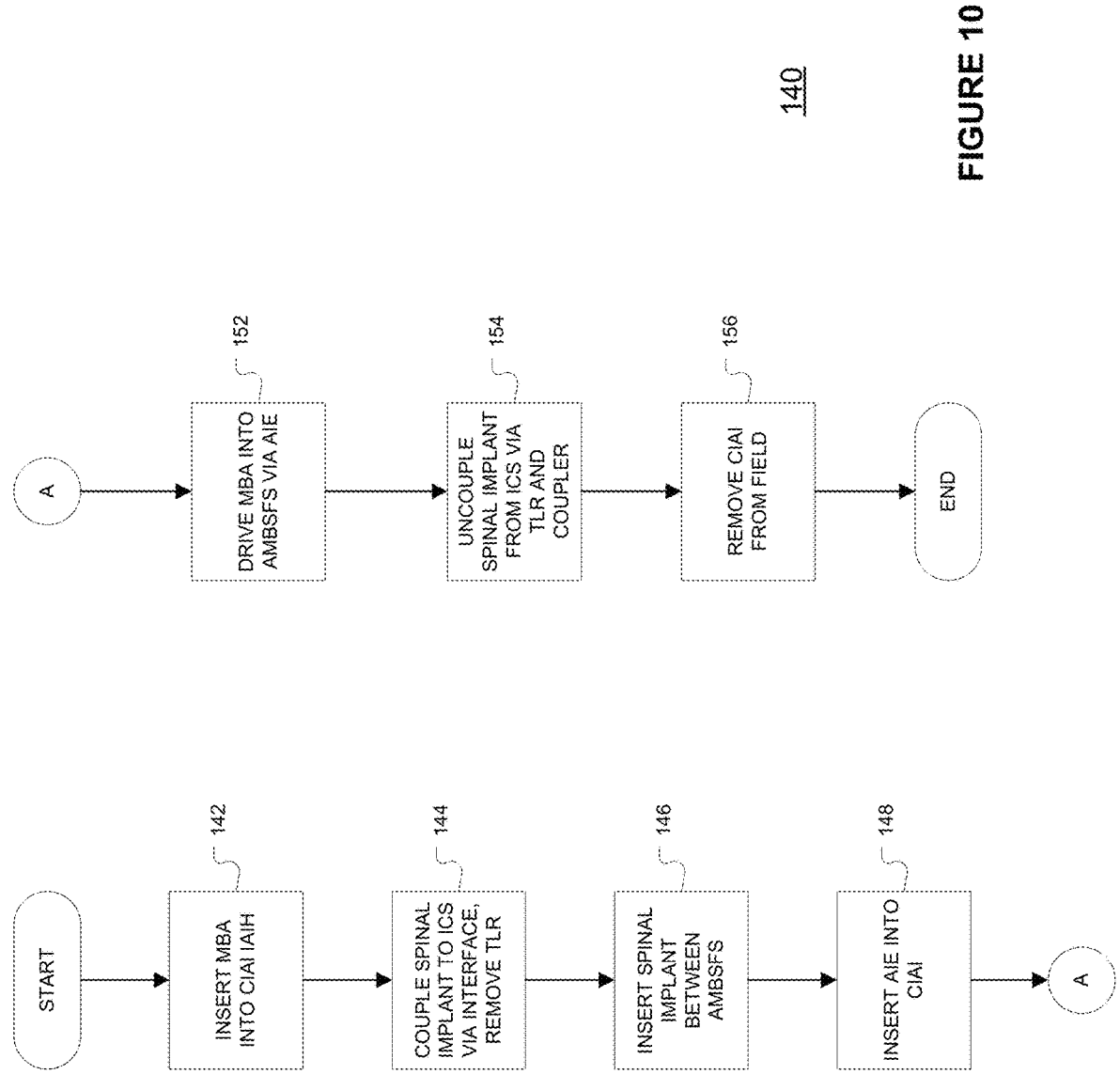
FIG. 10 is a diagram of algorithm for inserting an AMBSFS via CIAIA according to various embodiments.

Then as shown in FIG. 9F, a TLR 90 and a coupler 110 may be coupled to the combination implant and anchor inserter (CIAI) 60 with AIE 70 to decouple the IAIH 80 form an implant 30 per activity 154 of algorithm 140 according to various embodiments. The TLR 90 may be operatively coupled to the ICS 88 via the coupler 110, so the ICS 88 implant interface 88B may be decoupled from the implant's 30 threaded bore 34B per activity 154 of algorithm 140. Then the TLR 90, coupler 110, CIAI 60 with AIE 70 may be removed from the field as shown in FIG. 9G per activity 156 of algorithm 140.

When necessary to remove an inserted MBA 10, it may be ideally moved along the arc of the shaft 12 radius 17A shown in FIG. 1E. The removal tools 40A, 40B shown in FIGS. 4-5B may be coupled to an inserted MBA 10 via the tool's interface threads 48A, 48B to an inserted MBA 10 tool interface 16 internal threads 16B and be guided to the threads via the chamfer 16C and counterbore 16D. The tools 40A, B may then be used to remove an inserted MBA 10 at or near the arc 17A via the shafts 42A, 42B and handles 46A, 46B. As shown in FIG. 5B the tool 40B may be pivotable about two different axes 48A, 48B to ease the attachment to an inserted MBA 10 to be removed along the arc or radius 17A.

As noted, the geometry of the MBA 10 may provide greater expulsion strength and reliable cortical vertebral endplate penetration when inserted into vertebra 52A-C. In an embodiment, the MBA 10 outer surface may have scaling to provided increased osteointegration. The MBA 10 scallops 12A and undercuts 12B may also grip bone when inserted into thereto. The MBA 10 tip 18 structure may enable it to reliably penetrate cortical vertebral endplates without causing nor incurring fracture damage when be inserted into a vertebra 52A-C. In an embodiment, the MBA 10 may provide various fixation angles, convergent and/or divergent. In an embodiment, the MBA 10 and implant 30 may be formed of a biocompatible, substantially radiolucent material or complex of materials.

In an embodiment, the implant 30 may be formed of a polymer, ceramic, or combination of both, including Polyether ether ketone (PEEK) or other member of the polyaryletherketone family. The MBA 10 may be formed of a metal, alloy, or other osteoconductive material. In an embodiment, the MBA 10 may be formed from Titanium.

The accompanying drawings that form a part hereof show, by way of illustration and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In the foregoing Detailed Description, various features are grouped together in a single embodiment for the purpose of streamlining the disclosure. This method of disclosure is not to be interpreted to require more features than are expressly recited in each claim. Rather, inventive subject matter may be found in less than all features of a single disclosed embodiment. Thus, the following claims are hereby incorporated into the Detailed Description, with each claim standing on its own as a separate embodiment.

What is claimed is:

1. A combination implant and anchor inserter (CIAIS) that enables a user to insert an adjacent mammalian bony segments fixation system (AMBSFS) between first and second adjacent bony segments, the AMBSFS including an implant and at least two mammalian bony anchors (MBA), the implant including MBA interfaces for the two mammalian bony anchors, the CIAIS including:
  an implant and anchor insertion head (IAIH), the IAIH including:
    an implant connection system (ICS), the ICS couplable to an implant to be fixably inserted between the first and the second adjacent bony segments;
    a first insertion port sized to enable a first MBA to be inserted and stored therein;
    a second insertion port sized to enable a second MBA to be inserted and stored therein;
    a first ejection port coupled to the first insertion port, the first ejection port aligned with a first MBA interface of the implant when the implant is coupled to the ICS;
    a second ejection port coupled to the second insertion port, the second ejection port aligned with a second MBA interface of the implant when the implant is coupled to the ICS; and
    a first and a second MBA impact elements (AIE), each AIE including:
      a head;
      a distal section; and
      an elongate shaft between the head and the distal section,
      wherein the distal end is shaped to extend into an insertion port and engage an MBA base when placed adjacent thereto,
      wherein the AIE distal section includes:
        a proximal portion; and
        a distal portion,
        wherein the proximal portion has a larger cross-sectional area than the distal portion; and
        wherein the distal portion includes:
          a flat, upper distal end portion; and
          a slanted inward lower distal end portion.

2. The CIAIS of claim 1, wherein the CIAIS enables a user to fixably insert the implant between the first and the second adjacent bony segments, deploy the first MBA to couple the implant to the first bony segment, and deploy the second MBA to couple the implant to the second bony segment.

3. The CIAIS of claim 1, wherein the CIAIS enables a user to first fixably insert the implant between the first and the second adjacent bony segments and then simultaneously deploy the first MBA to couple the implant to the first bony segment and the second MBA to couple the implant to the second bony segment.

4. The CIAIS of claim 1, wherein the implant includes an internally threaded bore on a rear section and the ICS includes a threaded interface configured to be threadably securable and removable with the implant internally threaded bore.

5. The CIAIS of claim 4, wherein the implant includes a recess on its rear section leading to the internally threaded bore and the ICS includes an implant engagement protrusion shaped in relief of the implant recess and configured to nest therein when the implant is threadably coupled to the ICS threaded interface.

6. The CIAIS of claim 1, wherein the first insertion port and the second insertion port each include a MBA retention system (ARS), the ARS configured to securely and releasably engage an MBA base to hold a MBA within an insertion port until ejected from a corresponding ejection port.

7. The CIAIS of claim 6, wherein the ARS provides tactile feedback when an MBA is inserted into an insertion port and ejected from a corresponding ejection port.

8. The CIAIS of claim 7, wherein the ARS includes a deflectable wire.

9. The CIAIS of claim 8, wherein the deflectable wire is a nitinol wire.

10. The CIAIS of claim 1, wherein the distal portion is substantially rectangular in cross-section.

11. The CIAIS of claim 10, wherein the slanted inward lower distal end portion may engage an MBA base as the MBA is advanced through an insertion port.

12. The CIAIS of claim 11, wherein each AIE head has a flat portion perpendicular to the AIE elongated shaft.

13. The CIAIS of claim 1, wherein the slanted inward lower distal end portion is slanted about 45 degrees inward towards the proximal portion.

14. The CIAIS of claim 13, wherein each AIE head has a flat portion perpendicular to the AIE elongated shaft.

15. The CIAIS of claim 14, wherein the CIAIS enables a user to first fixably insert the implant between the first and the second adjacent bony segments and then simultaneously deploy the first MBA to couple the implant to the first bony segment and the second MBA to couple the implant to the second bony segment via the AIE.

16. The CIAIS of claim 1, wherein the insertion ports are sized to enable the AIE distal section distal portion to extend thereinto and engage an MBA stored therein while limiting the travel of the AIE with the IAIH.

17. The CIAIS of claim 1, wherein the insertion ports are sized to enable the AIE distal section distal portion to extend thereinto and engage an MBA stored therein while limiting the travel of the AIE distal section proximal portion therein.

18. The CIAIS of claim 1, wherein the flat, upper distal end portion may engage an MBA base when placed adjacent thereto.

* * * * *